(12) United States Patent
Polyak et al.

(10) Patent No.: US 8,034,561 B2
(45) Date of Patent: Oct. 11, 2011

(54) HIN-1, A TUMOR SUPPRESSOR GENE

(75) Inventors: Kornelia Polyak, Brookline, MA (US); Dennis Sgroi, Winchester, MA (US); Ian Krop, Boston, MA (US); Dale Porter, Boston, MA (US)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 12/627,939

(22) Filed: Nov. 30, 2009

(65) Prior Publication Data

US 2010/0273158 A1    Oct. 28, 2010

Related U.S. Application Data

(60) Continuation of application No. 10/982,142, filed on Nov. 5, 2004, now Pat. No. 7,625,715, which is a division of application No. 10/081,817, filed on Feb. 22, 2002, now Pat. No. 6,815,166.

(60) Provisional application No. 60/270,973, filed on Feb. 23, 2001, provisional application No. 60/351,908, filed on Jan. 25, 2002.

(51) Int. Cl.
  *C12Q 1/68* (2006.01)
  *C07H 21/04* (2006.01)

(52) U.S. Cl. ............ 435/6; 536/23.5

(58) Field of Classification Search .......... None
  See application file for complete search history.

(56) References Cited

U.S. PATENT DOCUMENTS 5,922,590 A    7/1999 Baylin et al.
7,282,207 B1   10/2007 Colpitts et al.

FOREIGN PATENT DOCUMENTS

WO    WO 98/33926    8/1998

OTHER PUBLICATIONS

Guo et al (Epigenetics, 2008, 3:336-341).*
Krop et al (Molecular Cancer Research, 2004, 2:489-494, IDS).*
Shigematsu et al (Int J Cancer, 2005, 113:600-604, IDS).*
Tisserand et al (Cancer Biology & Therapy, 2003, 2:559-563).*
iHOP, "SCGB3A1," p. 1-6.
iHOP, "HSHIN1", p. 1.
Biocompare, "HSHIN1", p. 1-3.
NCBI Sequence Deposit No. AI011836, Jun. 1998.
NCBI Sequence Deposit No. AF086152, Aug. 1998.
NCBI Sequence Deposit No. W34387, May 1996.
Greenbaum et al., Genome Biol., 2003, 4(9):117.1-117.8.
Krop et al., Mol. Cancer Research, 2004, 2:489-494.
Krop et al., HIN-1, a putative cytokine highly expressed in normal but not cancerous mammary epithelial cells, PNAS, 2001, 98(17):9796-9801.
Krop et al. II, Mol. Cancer Res., 2004, 9:489-494.
Porter et al., Expression of high in normal-1 (HIN-1) and uteroglobin related protein1—(UGRP-1) in adult and developing tissues, Mechanisms of Development, 2002, 114:201-204.
Shigematsu et al., Int. J. Cancer, 2005, 113:600-604.
Tockman et al., Cancer Res., 1992, 52:2711s-2718s.
Takahashi et al., Identification of tobacco HIN1 and two closely related genes as spermine-responsive genes and their differential expression during the Tobacco mosaic virus-induced hypersensitive response and during leaf—and flower-senescence, Plant Mol, Biol., 2004, 54:613-622.

* cited by examiner

*Primary Examiner* — Laura B Goddard
(74) *Attorney, Agent, or Firm* — Fish & Richardson P.C.

(57) ABSTRACT

The invention encompasses isolated DNAs encoding HIN-1 polypeptides, vectors containing such DNAs, cells containing the vectors, and isolated HIN-1 polypeptides. The invention also features methods of making and using HIN-1 polypeptides.

11 Claims, 17 Drawing Sheets

ATGAAGCTCGCCGCCCTCCTGGGGCTCTGCGTGGCCCTGTCCTGCAGCTCCGC
TCGTGCTTTCTTAGTGGGCTCGGCCAAGCCTGTGGCCCAGCCTGTCGCTGCGC
TGGAGTCGGCGGCGGAGGCCGGGGCCGGGACCCTGGCCAACCCCCTCGGCA
CCCTCAACCCGCTGAAGCTCCTGCTGAGCAGCCTGGGCATCCCCGTGAACCA
CCTCATAGAGGGCTCCCAGAAGTGTGTGGCTGAGCTGGGTCCCCAGGCCGTG
GGGGCCGTGAAGGCCCTGAAGGCCCTGCTGGGGGCCCTGACAGTGTTTGGC

FIG. 1A

CGTGCTTTCTTAGTGGGCTCGGCCAAGCCTGTGGCCCAGCCTGTCGCTGCGCT
GGAGTCGGCGGCGGAGGCCGGGGCCGGGACCCTGGCCAACCCCCTCGGCAC
CCTCAACCCGCTGAAGCTCCTGCTGAGCAGCCTGGGCATCCCCGTGAACCAC
CTCATAGAGGGCTCCCAGAAGTGTGTGGCTGAGCTGGGTCCCCAGGCCGTGG
GGGCCGTGAAGGCCCTGAAGGCCCTGCTGGGGGCCCTGACAGTGTTTGGC

FIG. 1B

TTCTTAGTGGGCTCGGCCAAGCCTGTGGCCCAGCCTGTCGCTGCGCTGGAGTC
GGCGGCGGAGGCCGGGGCCGGGACCCTGGCCAACCCCCTCGGCACCCTCAAC
CCGCTGAAGCTCCTGCTGAGCAGCCTGGGCATCCCCGTGAACCACCTCATAG
AGGGCTCCCAGAAGTGTGTGGCTGAGCTGGGTCCCCAGGCCGTGGGGGCCGT
GAAGGCCCTGAAGGCCCTGCTGGGGGCCCTGACAGTGTTTGGC

FIG. 1C

MKLAALLGLCVALSCSSARAFLVGSAKPVAQPVAALESAAEAGAGTLANPLGTL
NPLKLLLSSLGIPVNHLIEGSQKCVAELGPQAVGAVKALKALLGALTVFG

FIG. 2A

RAFLVGSAKPVAQPVAALESAAEAGAGTLANPLGTLNPLKLLLSSLGIPVNHLIE
GSQKCVAELGPQAVGAVKALKALLGALTVFG

FIG. 2B

FLVGSAKPVAQPVAALESAAEAGAGTLANPLGTLNPLKLLLSSLGIPVNHLIEGS
QKCVAELGPQAVGAVKALKALLGALTVFG

FIG. 2C

ATGAAGCTTACCACCACCTTTCTAGTGCTCTGTGTGGCTCTGCTCAGTGACTC
TGGTGTTGCTTTCTTCATGGACTCATTGGCCAAGCCTGCGGTAGAACCCGTGG
CCGCCCTTGCTCCAGCTGCAGAGGCTGTGGCAGGGGCTGTGCCTAGCCTACC
ATTAAGCCACTTGGCCATCCTGAGGTTCATCCTGGCCAGCATGGGCATCCCAT
TGGATCCTCTCATAGAGGGATCCAGGAAGTGTGTCACCGAGCTGGGCCCTGA
GGCTGTAGGAGCTGTGAAGTCACTGCTGGGGGTCCTGACAATGTTCGGT

FIG. 3A

GTTGCTTTCTTCATGGACTCATTGGCCAAGCCTGCGGTAGAACCCGTGGCCGC
CCTTGCTCCAGCTGCAGAGGCTGTGGCAGGGGCTGTGCCTAGCCTACCATTA
AGCCACTTGGCCATCCTGAGGTTCATCCTGGCCAGCATGGGCATCCCATTGG
ATCCTCTCATAGAGGGATCCAGGAAGTGTGTCACCGAGCTGGGCCCTGAGGC
TGTAGGAGCTGTGAAGTCACTGCTGGGGGTCCTGACAATGTTCGGT

FIG. 3B

TTCTTCATGGACTCATTGGCCAAGCCTGCGGTAGAACCCGTGGCCGCCCTTGC
TCCAGCTGCAGAGGCTGTGGCAGGGGCTGTGCCTAGCCTACCATTAAGCCAC
TTGGCCATCCTGAGGTTCATCCTGGCCAGCATGGGCATCCCATTGGATCCTCT
CATAGAGGGATCCAGGAAGTGTGTCACCGAGCTGGGCCCTGAGGCTGTAGGA
GCTGTGAAGTCACTGCTGGGGGTCCTGACAATGTTCGGT

FIG. 3C

MKLTTTFLVLCVALLSDSGVAFFMDSLAKPAVEPVAALAPAAEAVAGAVPSLPL
SHLAILRFILASMGIPLDPLIEGSRKCVTELGPEAVGAVKSLLGVLTMFG

FIG. 4A

VAFFMDSLAKPAVEPVAALAPAAEAVAGAVPSLPLSHLAILRFILASMGIPLDPLI
EGSRKCVTELGPEAVGAVKSLLGVLTMFG

FIG. 4B

FFMDSLAKPAVEPVAALAPAAEAVAGAVPSLPLSHLAILRFILASMGIPLDPLIEG
SRKCVTELGPEAVGAVKSLLGVLTMFG

CGGCCGGGGAGGCGGCCGGGAGTGAGGCCTGATCGTCCCTGGCGCCTCCACC
TCCCCAGGCGCAGAAGGCGCCCACGAGGACCCCCAGTGCCCGACGTTGCCAC
GGTCTGGGATCAGAGGCAGGGACCAGGGAGCCAGGAACTGCGCCGCCCCCG
CCCCTGCCCTGGCGCGAGGGAAGCTCCCTCACCNGAGGGAAGCTCCCCTCAC
CCGGCCCAGCCCTGCAGGGGGGCGCGTGGGGTCAGACCGCAAAGCGAAGGT
GCGGGCCGGGGTGGGCCTCGCGGAGACAAAGGCCGGGCCTGCCTCTCTCAGA
GGGCCCCAGCGCCTGCCAAGAGGAAGTCCTCGAGGCCCGGGCAGGGAAGGG
GGCACGGGCTTCCCAGGGCCCGCCGGCCGCAGCAGGAAGTTGGCCAGGGCA
CGGCCGTGAGCGGAGCGGGCAGGGCTTTCTCAGGAGCGCGGGCGAGGCCGG
CGCTGGAGGGGCGAGGACCGGGTATAAGAAGCCTCGTGGCCTTGCCCGGGC
AGCCGCAGGTTCCCCGCGCGCCCCGAGCCCCCGCGCC

FIG. 8

GTTCTCTGTTTTGTGTTGGTAGGCGTTGCTTTCTTGGTGGATTCACTGGCCAAG
CCTGTGGTAGAACCCGTGGCTGCCATTGCTACAGCTGCAGAGGCTGTGGCAG
GGCTGTGCCTAGCCTACCATTAAGCCACTTGGCCATCCTGAGGTTCATCGTG
ACCAGCCTGGGCATCCCATTGGATCCTCTCATAGATGGTTCCAGGAAGTGCGT
CACCGAGCTGGGCCCTGAGGCTGTAGGAGCTGTGAAGTCACTGCTGGGGGCC
CTGACAACGTTCGGT

FIG. 9A

VLCFVLVGVAFLVDSLAKPVVEPVAAIATAAEAVAGAVPSLPLSHLAILRFIVTSL
GIPLDPLIDGSRKCVTELGPEAVGAVKSLLGALTTFG

FIG. 9B

TTCTTGGTGGATTCACTGGCCAAGCCTGTGGTAGAACCCGTGGCTGCCATTGC
TACAGCTGCAGAGGCTGTGGCAGGGCTGTGCCTAGCCTACCATTAAGCCAC
TTGGCCATCCTGAGGTTCATCGTGACCAGCCTGGGCATCCCATTGGATCCTCT
CATAGATGGTTCCAGGAAGTGCGTCACCGAGCTGGGCCCTGAGGCTGTAGGA
GCTGTGAAGTCACTGCTGGGGCCCTGACAACGTTCGGT

FIG. 9C

FLVDSLAKPVVEPVAAIATAAEAVAGAVPSLPLSHLAILRFIVTSLGIPLDPLIDGS
RKCVTELGPEAVGAVKSLLGALTTFG

FIG. 9D

|           | | | | | | | | | | | | | | | | | | | | |
|---|---|---|---|---|---|---|---|---|---|---|---|---|---|---|---|---|---|---|---|---|
| Human HIN1 | M | K | I | A | - | L | I | G | L | C | V | A | L | S | C | S | S | A | R | P | L | V | G |
| Mouse HIN1 | M | K | I | T | T | F | L | V | T | C | V | I | L | S | D | S | Y | L | F | M | D |
| Rat HIN-1  |   |   |   |   |   | Y | L | C | F | V | L | V | G | - | - | V | A | P | L | V | D |
|            | M | K | L |   |   | L | V | L | C | V | A | L |   |   |   |   | V | A | F | L |   | D |

| Human HIN1 | S | - | A | K | P | V | A | Q | P | V | A | I | E | S | A | A | E | A | G | A | G | T | L | A |
| Mouse HIN1 | S | I | A | K | P | V | A | V | E | P | V | A | L | A | P | A | A | E | A | V | A | G | A | V | P |
| Rat HIN-1  | S | L | A | K | P | V | V | E | P | V | A | A | I | A | T | A | A | E | A | V | A | G | A | V | P |
|            | S | L | A | K | P | V | V | E | P | V | A | A | L | A |   | A | A | E | A | V | A | G | A | V | P |

| Human HIN1 | N | - | P | L | G | T | L | N | P | L | K | L | L | S | S | L | G | P | V | N | H | L | I |
| Mouse HIN1 | S | L | P | L | S | H | L | A | L | R | F | I | L | A | S | M | G | I | P | L | D | P | L | I |
| Rat HIN-1  | S | L | P | L | S | H | L | A | L | R | F | L | V | T | S | L | G | I | P | L | D | P | L | I |
|            | S | L | P | L | S | H | L | A | I | L | R | F | I | L | S |   | G | I | P | L | D | P | L | I |

| Human HIN1 | E | G | S | Q | K | C | V | A | E | T | G | P | Q | A | V | G | P | A | V | G | A | V | K | A | L | L |
| Mouse HIN1 | L | G | S | R | K | C | V | T | E | L | G | P | E | A | V | G | P | A | V | G | A | V | K | S | - | - | L | L |
| Rat HIN-1  | D | G | S | R | K | C | V | T | E | L | G | P | E | A | V | G | P | A | V | G | A | V | K | S | - | - | L | L |
|            | E | G | S | R | K | C | V | T | E | L | Q | P | E | A | V | G | A | V | G | A | V | K | S |   |   |   | L | L |

| Human HIN1 | G | A | I | T | V | F | G |
| Mouse HIN1 | G | V | L | T | M | F | G |
| Rat HIN-1  | G | A | L | T | I | F | G |
|            | G | A | L | T |   | F | G |

ATGTTCAAGCTGTCTGCCCTCGTTGTCCTGTGCGCTCTGGTGGCCTGCTCCTCG
GCTGAGCCCAAGCCCGCTATCCTGGCCGCCGCTCCAGTGGTTGCAGCTGCTCC
TGCCGGCGTGGTCACCGCTACCAGTTCGCAGTACGTGGCCCGCAACTTCAAC
GGTGTGGCTGCTGCTCCAGTTGTTGCCGCTGCCTACACCGCTCCAGTTGCCGC
CGCTGCCTATACCGCTCCAGTTGCCGCCGCTGCTTATACCGCTCCAGTTGCCG
CTGCCTACTCTGCTTATCCGTATGCCGCCTACCCTTACAGCGCTGCATACACC
ACTGTTTTG

FIG. 15

ATGAAATTCCTCGCCGTCTGCTTCTTCGCTGTTGTGGCTGTGGCTGCTGCCAA
ACCCGGTATTGTGGCTCCTCTGGCCTACACCGCTCCGGCTGTGGTGGGCAGTG
CCGCCTACGTGGCTCCCTACGCCTCCAGCTACACCGCCAACTCGGTGGCCCAC
AGCGCCGCCTTCCCAGCTGCCTACACCGCCGCCTACACTGCTCCCGTTGCTGC
TGCCTATACCGCTCCAGTGGCTGCTGCTTATACCGCTCCAGTGGCCGCTGCGT
ACGCCGCCCCAGCTGCCTATACCGCTGCCTACACCGCCCCCATTGCCCGTTAT
GCCGCCACCCCCTTCGCAGCACCCATCGCCGCTCCCGTGGCTGCCGCCTACAC
CGCCCCCATCGCCGCCGCTGCCCCAGTTCTGCTGAAGAAG

FIG. 16

SEQUENCE LISTING

```
<160> NUMBER OF SEQ ID NOS: 32

<210> SEQ ID NO 1
<211> LENGTH: 104
<212> TYPE: PRT
<213> ORGANISM: Homo sapiens

<400> SEQUENCE: 1

Met Lys Leu Ala Ala Leu Leu Gly Leu Cys Val Ala Leu Ser Cys Ser
 1               5                  10                  15

Ser Ala Arg Ala Phe Leu Val Gly Ser Ala Lys Pro Val Ala Gln Pro
            20                  25                  30

Val Ala Ala Leu Glu Ser Ala Ala Glu Ala Gly Ala Gly Thr Leu Ala
        35                  40                  45

Asn Pro Leu Gly Thr Leu Asn Pro Leu Lys Leu Leu Leu Ser Ser Leu
    50                  55                  60

Gly Ile Pro Val Asn His Leu Ile Glu Gly Ser Gln Lys Cys Val Ala
65                  70                  75                  80

Glu Leu Gly Pro Gln Ala Val Gly Ala Val Lys Ala Leu Lys Ala Leu
                85                  90                  95

Leu Gly Ala Leu Thr Val Phe Gly
            100

<210> SEQ ID NO 2
<211> LENGTH: 86
<212> TYPE: PRT
<213> ORGANISM: Homo sapiens
```

-continued

<400> SEQUENCE: 2

Arg Ala Phe Leu Val Gly Ser Ala Lys Pro Val Ala Gln Pro Val Ala
1               5                   10                  15

Ala Leu Glu Ser Ala Ala Glu Ala Gly Ala Gly Thr Leu Ala Asn Pro
            20                  25                  30

Leu Gly Thr Leu Asn Pro Leu Lys Leu Leu Leu Ser Ser Leu Gly Ile
        35                  40                  45

Pro Val Asn His Leu Ile Glu Gly Ser Gln Lys Cys Val Ala Glu Leu
    50                  55                  60

Gly Pro Gln Ala Val Gly Ala Val Lys Ala Leu Lys Ala Leu Leu Gly
65                  70                  75                  80

Ala Leu Thr Val Phe Gly
                85

<210> SEQ ID NO 3
<211> LENGTH: 312
<212> TYPE: DNA
<213> ORGANISM: Homo sapiens

<400> SEQUENCE: 3
atgaagctcg ccgccctcct ggggctctgc gtggccctgt cctgcagctc cgctcgtgct      60
ttcttagtgg gctcggccaa gcctgtggcc cagcctgtcg ctgcgctgga gtcggcggcg     120
gaggccgggg ccgggaccct ggccaacccc ctcggcaccc tcaacccgct gaagctcctg     180
ctgagcagcc tgggcatccc cgtgaaccac ctcatagagg ctcccagaa gtgtgtggct      240 gagctgggtc cccaggccgt gggggccgtg aaggccctga aggccctgct ggggccctg      300 acagtgtttg gc                                                         312

<210> SEQ ID NO 4
<211> LENGTH: 258
<212> TYPE: DNA
<213> ORGANISM: Homo sapiens

<400> SEQUENCE: 4
cgtgctttct agtgggctc ggccaagcct gtggcccagc ctgtcgctgc gctggagtcg      60
gcggcggagg ccggggccgg gaccctggcc aaccccctcg gcaccctcaa cccgctgaag     120
ctcctgctga gcagcctggg catccccgtg aaccacctca tagagggctc ccagaagtgt     180
gtggctgagc tgggtcccca ggccgtgggg gccgtgaagg ccctgaaggc cctgctgggg     240
gccctgacag tgtttggc                                                   258

<210> SEQ ID NO 5
<211> LENGTH: 104
<212> TYPE: PRT
<213> ORGANISM: Mus musculus

<400> SEQUENCE: 5

Met Lys Leu Thr Thr Thr Phe Leu Val Leu Cys Val Ala Leu Leu Ser
1               5                   10                  15

Asp Ser Gly Val Ala Phe Phe Met Asp Ser Leu Ala Lys Pro Ala Val
            20                  25                  30

Glu Pro Val Ala Ala Leu Ala Pro Ala Ala Glu Ala Val Ala Gly Ala
        35                  40                  45

Val Pro Ser Leu Pro Leu Ser His Leu Ala Ile Leu Arg Phe Ile Leu
    50                  55                  60

Ala Ser Met Gly Ile Pro Leu Asp Pro Leu Ile Glu Gly Ser Arg Lys
65                  70                  75                  80

```
Cys Val Thr Glu Leu Gly Pro Glu Ala Val Gly Ala Val Lys Ser Leu
                85                  90                  95

Leu Gly Val Leu Thr Met Phe Gly
            100
```

<210> SEQ ID NO 6
<211> LENGTH: 85
<212> TYPE: PRT
<213> ORGANISM: Mus musculus

<400> SEQUENCE: 6

```
Val Ala Phe Phe Met Asp Ser Leu Ala Lys Pro Ala Val Glu Pro Val
 1               5                  10                  15

Ala Ala Leu Ala Pro Ala Ala Glu Ala Val Ala Gly Ala Val Pro Ser
            20                  25                  30

Leu Pro Leu Ser His Leu Ala Ile Leu Arg Phe Ile Leu Ala Ser Met
            35                  40                  45

Gly Ile Pro Leu Asp Pro Leu Ile Glu Gly Ser Arg Lys Cys Val Thr
        50                  55                  60

Glu Leu Gly Pro Glu Ala Val Gly Ala Val Lys Ser Leu Leu Gly Val
65                  70                  75                  80

Leu Thr Met Phe Gly
                85
```

<210> SEQ ID NO 7
<211> LENGTH: 312
<212> TYPE: DNA
<213> ORGANISM: Mus musculus

<400> SEQUENCE: 7

```
atgaagctta ccaccacctt tctagtgctc tgtgtggctc tgctcagtga ctctggtgtt    60
gctttcttca tggactcatt ggccaagcct gcggtagaac ccgtggccgc ccttgctcca   120
gctgcagagg ctgtggcagg gctgtgcct agcctaccat taagccactt ggccatcctg   180
aggttcatcc tggccagcat gggcatccca ttggatcctc tcatagaggg atccaggaag   240
tgtgtcaccg agctgggccc tgaggctgta ggagctgtga agtcactgct ggggtcctg    300 acaatgttcg gt                                                       312
```

<210> SEQ ID NO 8
<211> LENGTH: 255
<212> TYPE: DNA
<213> ORGANISM: Mus musculus

<400> SEQUENCE: 8

```
gttgctttct tcatggactc attggccaag cctgcggtag aacccgtggc cgcccttgct    60
ccagctgcag aggctgtggc aggggctgtg cctagcctac cattaagcca cttggccatc   120
ctgaggttca tcctggccag catgggcatc ccattggatc tctcataga gggatccagg    180 aagtgtgtca ccgagctggg ccctgaggct gtaggagctg tgaagtcact gctgggggtc   240
ctgacaatgt tcggt                                                    255
```

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9

```
gagggaaagt tttttttatt tgg                                          23

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
caaaactaac aaacaaaac ca                                            22

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
gttaagagga agttttcgag gttc                                         24

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
ggtacgggtt ttttacggtt cgtc                                         24

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
aacttcttat acccgatcct cg                                           22

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
gttaagagga agttttgag gttt                                          24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
ggtatgggtt tttatggtt tgtt                                          24

<210> SEQ ID NO 16
<211> LENGTH: 25
<212> TYPE: DNA
<213> ORGANISM: Artificial Sequence
```

```
<220> FEATURE:
<223> OTHER INFORMATION: primer

<400> SEQUENCE: 16
caaaacttct tatacccaat cctca                                          25

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
tttccctgct tccacactag c                                              21

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
agattaagaa ggaattgacc t                                              21

<210> SEQ ID NO 19
<211> LENGTH: 551
<212> TYPE: DNA
<213> ORGANISM: Homo sapiens
<220> FEATURE:
<221> NAME/KEY: misc_feature
<222> LOCATION: 189
<223> OTHER INFORMATION: n = C or G

<400> SEQUENCE: 19
cggccgggga ggcggccggg agtgaggcct gatcgtccct ggcgcctcca cctccccagg     60
cgcagaaggc gcccacgagg accccccagtg cccgacgttg ccacggtctg ggatcagagg   120
cagggaccag ggagccagga actgcgccgc ccccgcccct gccctggcgc gagggaagct   180
ccctcaccng agggaagctc ccctcacccg gcccagccct gcaggggggc gcgtggggtc   240
agaccgcaaa gcgaaggtgc gggccggggt gggcctcgcg gagacaaagg ccgggcctgc   300
ctctctcaga gggccccagc gcctgccaag aggaagtcct cgaggccgg gcagggaagg    360 gggcacgggc ttcccaggge cgccggccg cagcaggaag ttggccaggg cacggccgtg   420
agcggagcgg gcagggcttt ctcaggagcg cgggcgaggc cggcgctgga ggggcgagga   480
ccgggtataa gaagcctcgt ggccttgccc gggcagccgc aggttccccg cgcgccccga   540 gccccgcgc c                                                         551

<210> SEQ ID NO 20
<211> LENGTH: 279
<212> TYPE: DNA
<213> ORGANISM: Rattus norvegicus

<400> SEQUENCE: 20
gttctctgtt ttgtgttggt aggcgttgct ttcttggtgg attcactggc caagcctgtg    60
gtagaacccg tggctgccat tgctacagct gcagaggctg tggcagggc tgtgcctagc   120 ctaccattaa gccacttggc catcctgagg ttcatcgtga ccagcctggg catcccattg   180
gatcctctca tagatggttc caggaagtgc gtcaccgagc tgggccctga ggctgtagga   240
gctgtgaagt cactgctggg ggccctgaca acgttcggt                          279
```

<210> SEQ ID NO 21
<211> LENGTH: 93
<212> TYPE: PRT
<213> ORGANISM: Rattus norvegicus

<400> SEQUENCE: 21

Val Leu Cys Phe Val Leu Val Gly Val Ala Phe Leu Val Asp Ser Leu
1               5                   10                  15

Ala Lys Pro Val Val Glu Pro Val Ala Ala Ile Ala Thr Ala Ala Glu
            20                  25                  30

Ala Val Ala Gly Ala Val Pro Ser Leu Pro Leu Ser His Leu Ala Ile
        35                  40                  45

Leu Arg Phe Ile Val Thr Ser Leu Gly Ile Pro Leu Asp Pro Leu Ile
    50                  55                  60

Asp Gly Ser Arg Lys Cys Val Thr Glu Leu Gly Pro Glu Ala Val Gly
65                  70                  75                  80

Ala Val Lys Ser Leu Leu Gly Ala Leu Thr Thr Phe Gly
                85                  90

<210> SEQ ID NO 22
<211> LENGTH: 84
<212> TYPE: PRT
<213> ORGANISM: Homo sapiens

<400> SEQUENCE: 22

Phe Leu Val Gly Ser Ala Lys Pro Val Ala Gln Pro Val Ala Ala Leu
1               5                   10                  15

Glu Ser Ala Ala Glu Ala Gly Ala Gly Thr Leu Ala Asn Pro Leu Gly
            20                  25                  30

Thr Leu Asn Pro Leu Lys Leu Leu Leu Ser Ser Leu Gly Ile Pro Val
        35                  40                  45

Asn His Leu Ile Glu Gly Ser Gln Lys Cys Val Ala Glu Leu Gly Pro
    50                  55                  60

Gln Ala Val Gly Ala Val Lys Ala Leu Lys Ala Leu Leu Gly Ala Leu
65                  70                  75                  80

Thr Val Phe Gly

<210> SEQ ID NO 23
<211> LENGTH: 252
<212> TYPE: DNA
<213> ORGANISM: Homo sapiens

<400> SEQUENCE: 23
ttcttagtgg gctcggccaa gcctgtggcc cagcctgtcg ctgcgctgga gtcggcggcg      60
gaggccgggg ccgggaccct ggccaacccc ctcggcaccc tcaacccgct gaagctcctg     120
ctgagcagcc tgggcatccc cgtgaaccac ctcatagagg gctcccagaa gtgtgtggct     180
gagctgggtc cccaggccgt gggggccgtg aaggccctga aggccctgct ggggccctg      240 acagtgtttg gc                                                         252

<210> SEQ ID NO 24
<211> LENGTH: 83
<212> TYPE: PRT
<213> ORGANISM: Mus musculus

<400> SEQUENCE: 24

Phe Phe Met Asp Ser Leu Ala Lys Pro Ala Val Glu Pro Val Ala Ala
1               5                   10                  15

```
Leu Ala Pro Ala Ala Glu Ala Val Ala Gly Ala Val Pro Ser Leu Pro
            20                  25                  30

Leu Ser His Leu Ala Ile Leu Arg Phe Ile Leu Ala Ser Met Gly Ile
        35                  40                  45

Pro Leu Asp Pro Leu Ile Glu Gly Ser Arg Lys Cys Val Thr Glu Leu
    50                  55                  60

Gly Pro Glu Ala Val Gly Ala Val Lys Ser Leu Leu Gly Val Leu Thr
65                  70                  75                  80

Met Phe Gly

<210> SEQ ID NO 25
<211> LENGTH: 249
<212> TYPE: DNA
<213> ORGANISM: Mus musculus

<400> SEQUENCE: 25
ttcttcatgg actcattggc caagcctgcg gtagaacccg tggccgccct tgctccagct      60
gcagaggctg tggcaggggc tgtgcctagc ctaccattaa gccacttggc catcctgagg     120
ttcatcctgg ccagcatggg catcccattg gatcctctca tagagggatc caggaagtgt     180
gtcaccgagc tgggccctga ggctgtagga gctgtgaagt cactgctggg ggtcctgaca     240
atgttcggt                                                             249

<210> SEQ ID NO 26
<211> LENGTH: 249
<212> TYPE: DNA
<213> ORGANISM: Rattus norvegicus

<400> SEQUENCE: 26
ttcttggtgg attcactggc caagcctgtg gtagaacccg tggctgccat tgctacagct      60
gcagaggctg tggcaggggc tgtgcctagc ctaccattaa gccacttggc catcctgagg     120
ttcatcgtga ccagcctggg catcccattg gatcctctca tagatggttc caggaagtgc     180
gtcaccgagc tgggccctga ggctgtagga gctgtgaagt cactgctggg ggccctgaca     240
acgttcggt                                                             249

<210> SEQ ID NO 27
<211> LENGTH: 83
<212> TYPE: PRT
<213> ORGANISM: Rattus norvegicus

<400> SEQUENCE: 27

Phe Leu Val Asp Ser Leu Ala Lys Pro Val Val Glu Pro Val Ala Ala
1               5                   10                  15

Ile Ala Thr Ala Ala Glu Ala Val Ala Gly Ala Val Pro Ser Leu Pro
            20                  25                  30

Leu Ser His Leu Ala Ile Leu Arg Phe Ile Val Thr Ser Leu Gly Ile
        35                  40                  45

Pro Leu Asp Pro Leu Ile Asp Gly Ser Arg Lys Cys Val Thr Glu Leu
    50                  55                  60

Gly Pro Glu Ala Val Gly Ala Val Lys Ser Leu Leu Gly Ala Leu Thr
65                  70                  75                  80

Thr Phe Gly

<210> SEQ ID NO 28
<211> LENGTH: 109
<212> TYPE: PRT
```

<213> ORGANISM: Drosophila melanogaster

<400> SEQUENCE: 28

Met Phe Lys Leu Ser Ala Leu Val Val Leu Cys Ala Leu Val Ala Cys
1               5                   10                  15

Ser Ser Ala Glu Pro Lys Pro Ala Ile Leu Ala Ala Ala Pro Val Val
            20                  25                  30

Ala Ala Ala Pro Ala Gly Val Val Thr Ala Thr Ser Ser Gln Tyr Val
        35                  40                  45

Ala Arg Asn Phe Asn Gly Val Ala Ala Ala Pro Val Val Ala Ala Ala
    50                  55                  60

Tyr Thr Ala Pro Val Ala Ala Ala Tyr Thr Ala Pro Val Ala Ala
65                  70                  75                  80

Ala Ala Tyr Thr Ala Pro Val Ala Ala Ala Tyr Ser Ala Tyr Pro Tyr
                85                  90                  95

Ala Ala Tyr Pro Tyr Ser Ala Ala Tyr Thr Thr Val Leu
            100                 105

<210> SEQ ID NO 29
<211> LENGTH: 327
<212> TYPE: DNA
<213> ORGANISM: Drosophila melanogaster

<400> SEQUENCE: 29
atgttcaagc tgtctgccct cgttgtcctg tgcgctctgg tggcctgctc ctcggctgag      60
cccaagcccg ctatcctggc cgccgctcca gtggttgcag ctgctcctgc cggcgtggtc     120
accgctacca gttcgcagta cgtggcccgc aacttcaacg gtgtggctgc tgctccagtt     180
gttgccgctg cctacaccgc tccagttgcc gccgctgcct ataccgctcc agttgccgcc     240
gctgcttata ccgctccagt tgccgctgcc tactctgctt atccgtatgc cgcctaccct     300
tacagcgctg catacaccac tgttttg                                         327

<210> SEQ ID NO 30
<211> LENGTH: 137
<212> TYPE: PRT
<213> ORGANISM: Drosophila melanogaster

<400> SEQUENCE: 30

Met Lys Phe Leu Ala Val Cys Phe Phe Ala Val Val Ala Val Ala Ala
1               5                   10                  15

Ala Lys Pro Gly Ile Val Ala Pro Leu Ala Tyr Thr Ala Pro Ala Val
            20                  25                  30

Val Gly Ser Ala Ala Tyr Val Ala Pro Tyr Ala Ser Ser Tyr Thr Ala
        35                  40                  45

Asn Ser Val Ala His Ser Ala Ala Phe Pro Ala Ala Tyr Thr Ala Ala
    50                  55                  60

Tyr Thr Ala Pro Val Ala Ala Ala Tyr Thr Ala Pro Val Ala Ala Ala
65                  70                  75                  80

Tyr Thr Ala Pro Val Ala Ala Tyr Ala Ala Pro Ala Ala Tyr Thr
                85                  90                  95

Ala Ala Tyr Thr Ala Pro Ile Ala Arg Tyr Ala Ala Thr Pro Phe Ala
            100                 105                 110

Ala Pro Ile Ala Ala Pro Val Ala Ala Ala Tyr Thr Ala Pro Ile Ala
        115                 120                 125

Ala Ala Ala Pro Val Leu Leu Lys Lys
    130                 135

```
<210> SEQ ID NO 31
<211> LENGTH: 411
<212> TYPE: DNA
<213> ORGANISM: Drosophila melanogaster

<400> SEQUENCE: 31
atgaaattcc tcgccgtctg cttcttcgct gttgtggctg tggctgctgc caaacccggt      60
attgtggctc ctctggccta caccgctccg gctgtggtgg gcagtgccgc ctacgtggct     120
ccctacgcct ccagctacac cgccaactcg gtggcccaca gcgccgcctt cccagctgcc     180
tacaccgccg cctacactgc tcccgttgct gctgcctata ccgctccagt ggctgctgct     240
tataccgctc cagtggccgc tgcgtacgcc gccccagctg cctataccgc tgcctacacc     300
gcccccattg cccgttatgc cgccacccccc ttcgcagcac ccatcgccgc tcccgtggct     360
gccgcctaca ccgcccccat cgccgccgct gccccagttc tgctgaagaa g             411

<210> SEQ ID NO 32
<211> LENGTH: 93
<212> TYPE: PRT
<213> ORGANISM: Homo sapiens

<400> SEQUENCE: 32

Met Lys Leu Val Thr Ile Phe Leu Leu Val Thr Ile Ser Leu Cys Ser
 1               5                  10                  15

Tyr Ser Ala Thr Ala Phe Leu Ile Asn Lys Val Pro Leu Pro Val Asp
            20                  25                  30

Lys Leu Ala Pro Leu Pro Leu Asp Asn Ile Leu Pro Phe Met Asp Pro
        35                  40                  45

Leu Lys Leu Leu Leu Lys Thr Leu Gly Ile Ser Val Glu His Leu Val
    50                  55                  60

Glu Gly Leu Arg Lys Cys Val Asn Glu Leu Gly Pro Glu Ala Ser Glu
65                  70                  75                  80

Ala Val Lys Lys Leu Leu Glu Ala Leu Ser His Leu Val
                85                  90
```

HIN-1, A TUMOR SUPPRESSOR GENE

This application is a continuation of U.S. patent application Ser. No. 10/982,142, filed Nov. 5, 2004, now U.S. Pat. No. 7,625,715, issued Dec. 1, 2009, which is a divisional of U.S. patent application Ser. No. 10/081,817, filed Feb. 22, 2002, now U.S. Pat. No. 6,815,166, issued Nov. 8, 2004, which claims priority of prior U.S. Provisional Applications 60/270,973, filed Feb. 23, 2001, and 60/351,908, filed Jan. 25, 2002. The disclosures of U.S. application Ser. No. 10/982, 142, U.S. application Ser. No. 10/081,817, U.S. Provisional Application 60/270,973, and U.S. Provisional Application No. 60/351,908 are incorporated herein by reference in their entirety.

TECHNICAL FIELD

The invention relates to cancer, and more particularly to cancer suppressor genes.

BACKGROUND

Breast carcinoma is the second leading cause of cancer-related death in women of the western world. In the United States alone over 175,000 new cases are diagnosed annually. The natural history of breast cancer involves a sequential progression through defined clinical and pathologic stages starting with initially benign then atypical hyperproliferation, progressing into in situ then invasive carcinomas, and culminating in metastatic disease. Ductal carcinoma in situ (DCIS) is the precursor of invasive ductal carcinoma.

SUMMARY

The invention is based on the identification of a human gene that, while highly expressed in normal breast tissue, is not expressed or is poorly expressed in DCIS tumors as well as breast tumors at other stages. This gene has been designated the "HIN-1" (High in Normal 1) gene. The inventors have also identified homologues of the human HIN-1 gene in mice and rats. Human HIN-1 is designated as hHIN-1, mouse HIN-1 as mHIN-1, and rat HIN-1 as rHIN-1. Text that refers to HIN-1 without specifying human, mouse or rat is pertinent to all three forms of HIN-1. The inventors have, in addition, identified two *Drosophila* genes containing sequences encoding proteins with significant homology to hHIN-1. Thus, the invention features an isolated DNA encoding an HIN-1 polypeptide, purified HIN-1 polypeptides, vectors containing the DNAs, and cells containing the vectors. In addition, the invention features a method of making an HIN-1 polypeptide, in vitro and in vivo methods of inhibiting proliferation of a cancer cell, and methods of diagnosing cancer.

More specifically, the invention features an isolated DNA containing a nucleic acid sequence encoding a polypeptide consisting of SEQ ID NO:1 or SEQ ID NO:22. The DNA can, for example, include the nucleic acid sequence designated SEQ ID NO:3 or SEQ ID NO:23. The invention also includes a vector containing: (a) a nucleic acid sequence that (i) encodes a polypeptide that inhibits proliferation of breast cancer cells, and (ii) hybridizes under highly stringent conditions to a probe consisting of a sequence that is the complement of SEQ ID NO:3; or (b) the complement of the nucleic acid sequence. Vectors of the invention can also contain any of the isolated DNAs of the invention. In the vectors, polypeptide encoding sequences can be operably linked to a transcriptional regulatory element (TRE). Also encompassed by the invention is a cell (e.g., a prokaryotic or a eukaryotic cell) comprising any vector of the invention.

Also featured by the invention is an isolated polypeptide containing: (a) a protein that inhibits proliferation of breast cancer cells and that is encoded by a nucleic acid sequence that hybridizes under highly stringent conditions to a probe that includes or is the sequence that is the complement of SEQ ID NO:3; or (b) the protein, except for one or more conservative amino acid substitutions. The polypeptide can include the amino acid sequence of SEQ ID NO:1 or SEQ ID NO:22. Another polypeptide of the invention is an isolated polypeptide containing (a) a functional fragment of any of the above-described polypeptides; or (b) the functional fragment, except for one or more conservative amino acid substitutions. Also included in the invention is a method of making a polypeptide; the method involves culturing a cell of the invention and extracting the polypeptide from the culture. The invention also features fragments of any of the DNAs of the invention, e.g., fragments of the DNA with SEQ ID NO:3 that include nucleotides 55 and 56 of SEQ ID NO:3. The fragments of the DNAs of the invention will be at least 10 bp, 15 bp, 25 bp, 50 bp, 75 bp, 100 bp, 125 bp, 150 bp, 175 bp, 200 bp, 250 bp, 300 bp, 305 bp, or 309 by long.

Another aspect of the invention is a method of inhibiting proliferation of a cancer cell. The method involves contacting the cancer cell with any of the polypeptides of the invention. The cancer cell can be, for example, a breast cancer cell. The contacting can be in vitro. Alternatively, the cancer cell can be in a mammal and the contacting in the mammal can involve administering either the polypeptide or a polynucleotide encoding the polypeptide to the mammal. Where the cancer cell is in a mammal, the method can involve:

(a) providing a recombinant cell that is the progeny of a cell obtained from the mammal and has been transfected or transformed ex vivo with a nucleic acid encoding the polypeptide; and
(b) administering the cell to the mammal.

Another embodiment of the invention is a method of identifying a compound that enhances inhibition of proliferation of cancer cells. The method involves: (a) providing a first and a second plurality of cancer cells; (b) combining a test compound, the first plurality of cancer cells, and any of the polypeptides of the invention; (c) combining the second plurality of cancer cells and; (d) determining the level proliferation of the first plurality of cancer cells. A decreased level of proliferation of the first plurality of cancer cells, as compared to the second plurality of cells, indicates that the test compound enhances inhibition of proliferation of cancer cells by the polypeptide.

Also featured by the invention is a method of diagnosis. The method can involve (a) providing a test cell; and b) measuring the level of expression of a HIN-1 gene in the cell. Lack of expression of the HIN-1 gene or a low level of expression of the HIN-1 gene is an indication that the test cell is a cancer cell. Expression of the HIN-1 gene can be measured as a function of the level of HIN-1 mRNA in the cell or as a function of the level of HIN-1 polypeptide in the cell.

In another aspect, the invention provides a method of diagnosis. The method involves (a) providing a test cell; and (b) determining the degree of methylation of a HIN-1 promoter region in the test cell. A high degree of methylation of the HIN-1 promoter region is an indication that the test cell is a cancer cell. The test cell can be, for example, a breast cell, a prostate cell, a pancreatic cell, or a lung cell.

The invention features an antibody that binds to any of the polypeptides of invention. The antibody can be a monoclonal antibody or a polyclonal antibody.

Also included in the invention is a method of treatment that involves identifying a patient as having cancer cells in which (a) HIN-1 gene expression is low or (b) a HIN-1 promoter region is methylated; and treating the patient with a compound that reduces methylation of the HIN-1 promoter region or with a compound that induces expression of a gene with a methylated promoter region, e.g., the HIN-1 gene.

Yet another aspect of the invention is a method of identifying a compound that replaces the function of HIN-1 in cells that do not express HIN-1. The method involves:
(a) providing a first cell that does not express HIN-1; (b) providing a second cell that does express HIN-1; (c) treating the first cell and the second cell with a test compound; and
(d) determining whether the test compound decreases proliferation of the first or the second cell. A compound that decreases proliferation of the first cell but not the second cell can potentially replace the function of HIN-1 in cells that do not express HIN-1.

"Polypeptide" and "protein" are used interchangeably and mean any peptide-linked chain of amino acids, regardless of length or post-translational modification. The invention also features HIN-1 polypeptides with conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, "full-length HIN-1" is HIN-1 with its native signal sequence.

The term "isolated" polypeptide or peptide fragment as used herein refers to a polypeptide or a peptide fragment which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue, or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide is "isolated."

An isolated polypeptide (or peptide fragment) of the invention can be obtained, for example, by extraction from a natural source (e.g., from tissues or bodily fluids); by expression of a recombinant nucleic acid encoding the polypeptide; or by chemical synthesis. A polypeptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

An "isolated DNA" is either (1) a DNA that contains sequence not identical to that of any naturally occurring sequence, or (2), in the context of a DNA with a naturally-occurring sequence (e.g., a cDNA or genomic DNA), a DNA free of at least one of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. The term also includes a separate molecule such as: a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein. Also included is a recombinant DNA that includes a portion of SEQ ID NO:3, SEQ ID NO:7, or SEQ ID NO:20. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

As used herein, a "functional fragment" of a HIN-1 polypeptide is a fragment of the polypeptide that is shorter than the full-length polypeptide and has at least 5% (e.g., 10%, 20%, 30%, 40%, 50%, 60%, 70%, 80%, 90%, 95%, 98%, 99%, 100%, or more) of the ability of the full-length polypeptide to inhibit the proliferation of a cancer cell, e.g., a breast cancer cell. Fragments of interest can be made either by recombinant, synthetic, or proteolytic digestive methods. Such fragments can then be isolated and tested for their ability to inhibit the proliferation of cancer cells as measured by [$^3$H]-thymidine incorporation or cell counting.

As used herein, "operably linked" means incorporated into a genetic construct so that expression control sequences effectively control expression of a coding sequence of interest.

As used herein, the term "antibody" refers not only to whole antibody molecules, but also to antigen-binding fragments, e.g., Fab, F(ab')$_2$, Fv, and single chain Fv (ScFv) fragments. Also included are chimeric antibodies.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inhibiting proliferation of cancer cells, will be apparent from the following description, from the drawings and from the claims.

DESCRIPTION OF DRAWINGS

FIG. 1A is a depiction of the nucleotide sequence (SEQ ID NO:3) of cDNA encoding the full-length hHIN-1 polypeptide.

FIG. 1B is a depiction of the nucleotide sequence (SEQ ID NO:4) of cDNA encoding a mature hHIN-1 polypeptide (i.e., the full-length hHIN-1 polypeptide but without an 18 amino acid signal peptide).

FIG. 1C is a depiction of the nucleotide sequence (SEQ ID NO:23) of cDNA encoding a mature hHIN-1 polypeptide (i.e., the full-length hHIN-1 polypeptide but without a 20 amino acid signal peptide).

FIG. 2A is a depiction of the amino acid sequence (SEQ ID NO:1) of the full-length hHIN-1 polypeptide.

FIG. 2B is a depiction of the amino acid sequence (SEQ ID NO:2) of a mature hHIN-1 polypeptide (i.e., the full-length hHIN-1 polypeptide but without an 18 amino acid signal peptide).

FIG. 2C is a depiction of the amino acid sequence (SEQ ID NO:22) of a mature hHIN-1 polypeptide (i.e., the full length hHIN-1 polypeptide but without a 20 amino acid signal peptide).

FIG. 3A is a depiction of the nucleotide sequence (SEQ ID NO:7) of cDNA encoding the full-length mHIN-1 polypeptide.

FIG. 3B is a depiction of the nucleotide sequence (SEQ ID NO:8) of cDNA encoding a mature mHIN-1 polypeptide (i.e., the full-length mHIN-1 polypeptide but without a 19 amino acid signal peptide).

FIG. 3C is a depiction of the nucleotide sequence (SEQ ID NO:25) of cDNA encoding a mature mHIN-1 polypeptide (i.e., the full-length mHIN-1 polypeptide but without a 21 amino acid signal peptide).

FIG. 4A is a depiction of the amino acid sequence (SEQ ID NO:5) of the full-length mHIN-1 polypeptide.

FIG. 4B is a depiction of the amino acid sequence (SEQ ID NO:6) of a mature mHIN-1 polypeptide (i.e., the full-length mHIN-1 polypeptide but without a 19 amino acid signal peptide).

FIG. 4C is a depiction of the amino acid sequence (SEQ ID NO:24) of a mature mHIN-1 polypeptide (i.e., the full-length mHIN-1 polypeptide but without a 21 amino acid signal peptide).

FIG. 5C), normal mammary epithelium (200× magnification; FIG. 5D) and DCIS mammary epithelium (200× magnification; FIG. 5E).

FIG. 6B is a photograph of an ethidium bromide stained elecrophoretic gel of samples from an RT-PCR analysis of hHIN-1 mRNA in the indicated breast cancer cell lines that were cultured in the presence ("+") and absence ("−") of 5aza-C.

FIG. 6C is a photograph of an ethidium bromide stained elecrophoretic gel of samples from a methylation-specific PCR analysis of the hHIN-1 proximal promoter region in genomic DNA from a series of primary breast tumors (upper panel) and breast cancer cell lines (lower panel). "M" and "U" indicate PCRs performed with methylated and the unmethylated sequence-specific primers, respectively.

FIG. 7 is a photograph of a Western blot. Cell lysates or culture media separated from cells were incubated with nickel-containing Ni-NTA beads. Proteins bound to beads were eluted from the beads and subjected to sodium dodecyl sulfate polyacrylamide electrophoresis (SDS-PAGE) and the SDS-PAGE gel was blotted onto a Western blot membrane which was developed with a rabbit polyclonal antibody specific for hHIN-1. The cells and culture media tested were from cultures containing: (i) 293 cells (first four lanes) transfected with pCEP4 ("C"), or pCEP4-Histag-HIN-1 constructs; or (ii) MCF10A or SUM159 cells infected with Ad-Track-GFP ("G") or Ad-Track-Histag-HIN-1 ("H") adenoviral vectors.

FIG. 8. is a depiction of the nucleotide sequence (SEQ ID NO:19) of a promoter region immediately 5' of the coding sequence for the hHIN-1 polypeptide.

FIG. 9A is a depiction of the nucleotide sequence (SEQ ID NO:20) of 279 nucleotides of cDNA encoding 93 amino acid of the full-length rHIN-1 polypeptide.

FIG. 9B is a depiction of the amino acid sequence (SEQ ID NO:21) of 93 amino acids of the full-length rHIN-1 polypeptide.

FIG. 9C is a depiction of the nucleotide sequence (SE ID NO:26) of cDNA encoding a mature rHIN-1 polypeptide (i.e., the full length rHIN-1 polypeptide but without a signal peptide).

FIG. 9D is a depiction of the amino acid sequence (SEQ ID NO:27) of a mature rHIN-1 polypeptide (i.e., the full-length rHIN-1 polypeptide but without a signal peptide).

FIG. 10 is a depiction of the amino acid sequences of hHIN-1 ("Human HIN1"), (SEQ ID NO:1) mHIN-1 ("Mouse HIN1") (SEQ ID NO:5) and 93 amino acids of rHIN-1 ("Rat HIN1") (SEQ ID NO:21) aligned for maximal homology. Amino acid residues common to more than one of the polypeptide are indicated at the relevant position under the sequences. Conserved residues and identical residues are shaded. Possible N-terminal signal peptides are indicated by a bold line and corresponding signal peptide cleavage sites are indicated by an arrow.

In FIG. 11D the "Involuting D21.A" and "Involuting D21.B" mammary glands were obtained from two independent mice at 21 days post partum.

FIG. 14A is a depiction of the amino acid sequences of: human UGRP-1 (SEQ ID NO:32); hHIN-1 (SEQ ID NO:1); the *Drosophila* GC130681 protein (SEQ ID NO:28); and the *Drosophila* GC13674 protein (SEQ ID NO:30) aligned for optimal homology using MacVector3 software. Identical and conserved amino acids are indicated with dark shading and light shading, respectively.

FIG. 15 is a depiction of the nucleotide sequence of cDNA (SEQ ID NO:29) encoding the *Drosophila* GC130681 protein.

FIG. 16 is a depiction of the nucleotide sequence of cDNA (SEQ ID NO:31) encoding the *Drosophila* GC13674 protein.

DETAILED DESCRIPTION

Figure 5A:
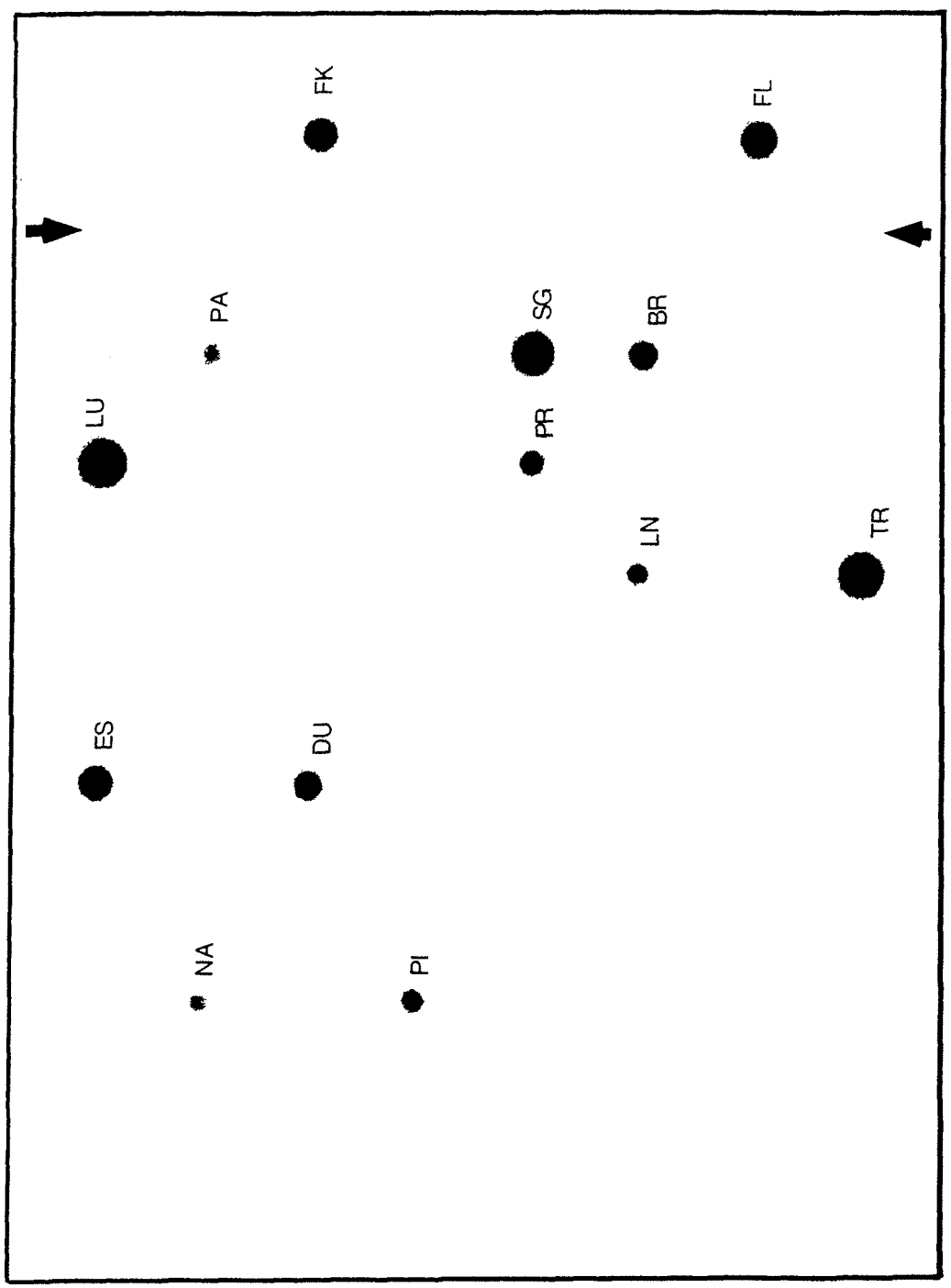
FIG. 5A is a photograph of an autoradiogram obtained from a multiple tissue mRNA expression array exposed to a $^{32}$P-labeled hHIN-1 cDNA probe (BR, breast; LU, lung; ES, esophagus; DU, duodenum; TR, trachea; PR, prostate; FL, fetal lung; FK, fetal kidney; PA, pancreas; LN, lymph nodes; NA, nucleus accumbens; and PI, pituitary gland). The arrows indicate the position of a row of spots of mRNA from a range of cancer lines including leukemias, lymphomas, lung cancer cells, colorectal cancer cells, and cervical cancer cells.

Using the Serial Analysis of Gene Expression (SAGE) methodology, the inventors have identified a gene, the hHIN-1 gene, that is expressed in normal human mammary epithelial tissue, but either is not or is weakly expressed in the majority of breast carcinomas. Inspection of the nucleotide sequence of a cDNA clone that contained a region of 100% homology to the hHIN-1 tag identified by the SAGE methodology revealed that the cDNA clone included a sequence (SEQ ID NO:3) encoding a polypeptide (the hHIN-1 polypeptide; SEQ ID NO:1) (FIG. 2A) of 104 amino acid residues in length. Inspection of the hHIN-1 polypeptide's amino acid sequence revealed the presence of two possible signal peptide cleavage sites, one after $Ala_{18}$ and another after $Ala_{20}$. Thus, the signal peptide can be either 18 or 20 amino acids long. The amino acid sequence of the mature hHIN-1 polypeptide lacking the 18 amino acid signal peptide is assigned SEQ ID NO:2 (FIG. 2B) and the nucleotide sequence of cDNA encoding this mature hHIN-1 polypeptide is assigned SEQ ID NO:4 (FIG. 1B). The amino acid sequence of the mature hHIN-1 polypeptide lacking the 20 amino acid signal peptide is assigned SEQ ID NO:22 (FIG. 2C) and the nucleotide sequence of cDNA encoding this mature hHIN-1 polypeptide is assigned SEQ ID NO:23 (FIG. 1C). The presence of a signal peptide and a transfection analysis indicated that the hHIN-1 polypeptide is a novel cytokine that inhibits the growth of at least some breast cancer cells. The inventors have also identified a mouse cDNA homologue (mHIN-1) of hHIN-1 cDNA that encodes a polypeptide (the mHIN-1 polypeptide) of the same length as hHIN-1. The full-length mHIN-1 polypeptide is assigned SEQ ID NO:5 (FIG. 4A) and the cDNA encoding the full-length mHIN-1 polypeptide is assigned SEQ ID NO:7 (FIG. 3A). Two possible signal peptides were identified within the mHIN-1 full-length polypeptide, one of 19 and 21 amino acids in length. The amino acid sequence of the mature mHIN-1 polypeptide lacking the 19 amino acid signal peptide is assigned SEQ ID NO:6 (FIG. 4B) and the nucleotide sequence of cDNA encoding this mature mHIN-1 polypeptide is assigned SEQ ID NO:8 (FIG. 3B). The amino acid sequence of mature mHIN-1 polypeptide lacking the 21 amino acid signal is assigned SEQ ID NO:24 (FIG. 4C) and the nucleotide sequence of cDNA encoding this mature mHIN-1 polypeptide is assigned SEQ ID NO:25 (FIG. 3C). In addition, the inventors have defined a rat partial cDNA sequence (SEQ ID NO:20) (FIG. 9A) encoding a large portion of the rat homologue (rHIN-1) (SEQ ID NO:21) (FIG. 9B) of hHIN-1. A signal peptide cleavage site was identified. The amino acid sequence of the mature rHIN-1 polypeptide lacking the signal peptide is assigned SEQ ID NO:27 (FIG. 9D) and the nucleotide sequence of cDNA encoding this mature rHIN-1 polypeptide is assigned SEQ ID NO:26 (FIG. 9C).

RNA hybridization studies showed that the hHIN-1 gene is expressed highly in a number of other normal tissues, e.g., lung, trachea, salivary gland, prostate gland, esophagus, duodenum, fetal lung, and fetal kidney. Lower expression of the hHIN-1 gene was seen in pancreas, pituitary gland, lymph node, and accumbens nucleus. Dramatically reduced expression of hHIN-1 RNA (compared to normal lung tissue) was seen in 40 primary lung tumors. Loss of hHIN-1 expression in breast cancer was not due to mutational events, but rather, at least in the majority of breast cancer cells in which lack of or decreased HIN-1 gene expression was seen, was due to methylation of a CpG island in the hHIN-1 gene promoter region. Similarly, dramatically reduced hHIN-1 expression was seen in a panel of human lung cancers and methylation of the hHIN-1 gene promoter region was observed in five out of nine lung tumors tested. Similar results were obtained with prostate and pancreatic cancer cells.

Developmental studies and the expression pattern in *Drosophila* of two proteins (protein GC130681 and protein GC13674) with low but significant amino acid homology to hHIN-1 indicate an evolutionarily conserved role for HIN-1 in epithelial cell differentiation.

HIN-1 Nucleic Acid Molecules

The HIN-1 nucleic acid molecules of the invention can be cDNA, genomic DNA, synthetic DNA, or RNA, and can be double-stranded or single-stranded (i.e., either a sense or an antisense strand). Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOS:1 and 5). In addition, these nucleic acid molecules are not limited to coding sequences, e.g., they can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. The nucleic acids can be those of a human, non-human primate (e.g., monkey), mouse, rat, guinea pig, cow, sheep, horse, pig, rabbit, dog, or cat. Combinations or modifications of the nucleotides within these types of nucleic acids are also encompassed.

In addition, the isolated nucleic acid molecules of the invention encompass segments that are not found as such in the natural state. Thus, the invention encompasses recombinant nucleic acid molecules (for example, isolated nucleic acid molecules encoding hHIN-1 or mHIN-1) incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

Techniques associated with detection or regulation of genes are well known to skilled artisans. Such techniques can be used to diagnose and/or treat disorders associated with aberrant HIN-1 expression. Nucleic acid molecules of the invention are discussed further below in the context of their therapeutic utility.

A HIN-1 family gene or protein can be identified based on its similarity to the relevant HIN-1 gene or protein, respectively. For example, the identification can be based on sequence identity. The invention features isolated nucleic acid molecules which are at least 50% (or 55%, 65%, 75%, 85%, 95%, or 98%) identical to: (a) a nucleic acid molecule that encodes the polypeptide of SEQ ID NOS: 1, 2, 5, 6, 21, 22, 24, or 27; (b) the nucleotide sequence of SEQ ID NOS: 3, 4, 7, 8, 20, 23, 25, or 26; and (c) a nucleic acid molecule which includes a segment of at least 30 (e.g., at least 40, 50, 60, 80, 100, 125, 150, 175, 200, 250, 300, or 306) nucleotides of SEQ ID NO: 3, 7, or 20.

The determination of percent identity between two sequences is accomplished using the mathematical algorithm of Karlin and Altschul, *Proc. Natl. Acad. Sci. USA* 90, 5873-5877, 1993. Such an algorithm is incorporated into the BLASTN and BLASTP programs of Altschul et al. (1990) *J. Mol. Biol.* 215, 403-410. BLAST nucleotide searches are performed with the BLASTN program, score =100, wordlength =12, to obtain nucleotide sequences homologous to HIN-1-encoding nucleic acids. BLAST protein searches are performed with the BLASTP program, score =50, wordlength =3, to obtain amino acid sequences homologous to the HIN-1 polypeptide. To obtain gapped alignments for comparative purposes, Gapped BLAST is utilized as described in Altschul et al. (1997) *Nucleic Acids Res.* 25, 3389-3402. When utilizing BLAST and Gapped BLAST programs, the default parameters of the respective programs (e.g., XBLAST and NBLAST) are used.

Hybridization can also be used as a measure of homology between two nucleic acid sequences. A HIN-1-encoding nucleic acid sequence, or a portion thereof, can be used as a hybridization probe according to standard hybridization techniques. The hybridization of a HIN-1 probe to DNA or RNA from a test source (e.g., a mammalian cell) is an indication of the presence of HIN-1 DNA or RNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The invention also encompasses: (a) vectors (see below) that contain any of the foregoing HIN-1-related coding sequences and/or their complements (that is, "antisense" sequences); (b) expression vectors that contain any of the foregoing HIN-1-related coding sequences operably linked to any transcriptional/translational regulatory elements (examples of which are given below) necessary to direct expression of the coding sequences; (c) expression vectors encoding, in addition to a HIN-1 polypeptide, a sequence unrelated to HIN-1, such as a reporter, a marker, or a signal peptide fused to HIN-1; and (d) genetically engineered host cells (see below) that contain any of the foregoing expression vectors and thereby express the nucleic acid molecules of the invention.

Recombinant nucleic acid molecules can contain a sequence encoding HIN-1 or HIN-1 having an heterologous signal sequence. The full length HIN-1 polypeptide, or a fragment thereof, may be fused to such heterologous signal sequences or to additional polypeptides, as described below. Similarly, the nucleic acid molecules of the invention can encode the mature form of HIN-1 or a form that includes an exogenous polypeptide that facilitates secretion.

The transcriptional/translational regulatory elements referred to above and further described below include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a HIN-1 polypeptide and the second portion being, for example, the reporter described above or an Ig constant region or part of an Ig constant region, e.g., the CH2 and CH3 domains of IgG2a heavy chain. Other hybrids could include an antigenic tag or His tag to facilitate purification.

The expression systems that may be used for purposes of the invention include but are not limited to microorganisms such as bacteria (for example, *E. coli* and *B. subtilis*) to transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecule of the invention; insect cell systems infected with recombinant virus expression vectors (for example, baculovirus) containing the nucleic acid molecule of the invention; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a HIN-1 nucleotide sequence; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Polypeptides and Polypeptide Fragments

The polypeptides of the invention include all those disclosed herein. They can be, for example, hHIN-1 (SEQ ID NO:1), hHIN-1 without a signal peptide (SEQ ID NO:2 or SEQ ID NO:22), mHIN-1 (SEQ ID NO:5), mHIN-1 without a signal peptide (SEQ ID NO:6 or SEQ ID NO:24), most of rHIN-1 (SEQ ID NO:21), rHIN-1 without a signal peptide (SEQ ID NO:27) and functional fragments of these polypeptides. The polypeptides embraced by the invention also include fusion proteins that contain either full-length HIN-1 or a functional fragment of it fused to unrelated amino acid sequence. The unrelated sequences can be additional functional domains or signal peptides. Signal peptides are described in greater detail and exemplified below. The polypeptides can be any of those described above but with one or more (e.g., one, two, three, four, five, six, seven, eight, nine, 10, 12, 14, 17, 20, 25, 30, 35, 40, 50, 60, 70, 80, 90, 100 or more) conservative substitutions.

The polypeptides can be purified from natural sources (e.g., blood, serum, plasma, tissues or cells such as normal breast epithelial cells or any cell that naturally produces HIN-1 polypeptides). Smaller peptides (less than 50 amino acids long) can also be conveniently synthesized by standard chemical means. In addition, both polypeptides and peptides can be produced by standard in vitro recombinant DNA techniques and in vivo transgenesis, using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

Polypeptides and fragments of the invention also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the functional peptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to inhibit the proliferation of cancer cells (e.g., breast cancer cells) in a manner qualitatively identical to that of the HIN-1 functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Inhibiting Proliferation of a Cancer Cell

The methods of the invention involve contacting a cancer cell with a HIN-1 polypeptide of the invention, or a functional fragment thereof, in order to inhibit proliferation of the cancer cell. Such polypeptides or functional fragments can have amino acid sequences identical to wild-type sequences or they can contain one or more (e.g., two, three, four, five, six, seven, eight, nine, 10, 12, 14, 17, 20, 25, 30, 35, 40, 50, 60, 70, 80, 90, 100 or more) conservative amino acid substitutions. Cancer cells can be breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cells.

The methods can be performed in vitro, in vivo, or ex vivo. In vitro application of HIN-1 can be useful, for example, in basic scientific studies of tumor cell biology, e.g., studies on signal transduction or cell cycle analysis. In addition, HIN-1 and the polynucleotides of the invention (DNA and/or RNA) can be used as "positive controls" in diagnostic assays (see below). However, the methods of the invention will preferably be in vivo or ex vivo (see below).

The HIN-1 proteins and variants thereof are generally useful as cancer cell (e.g., breast cancer cell) proliferation-inhibiting therapeutics. They can be administered to mammalian subjects (e.g., human breast cancer patients) alone or in conjunction with such drugs and/or radiotherapy.

These methods of the invention can be applied to a wide range of species, e.g., humans, non-human primates, horses, cattle, pigs, sheep, goats, dogs, cats, rabbits, guinea pigs, hamsters, rats, and mice.

In Vivo Approaches

In one in vivo approach, the HIN-1 polypeptide (or a functional fragment thereof) itself is administered to the subject. Generally, the compounds of the invention will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. They are preferably delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 μg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding a HIN-1 polypeptide or functional fragment can be delivered to cancer cells in a mammal. Expression of the coding sequence will preferably be directed to lymphoid tissue of the subject by, for example, delivery of the polynucleotide to the lymphoid tissue. Expression of the coding sequence can be directed to any cell in the body of the subject. However, expression will preferably be directed to cells in the vicinity of the tumor cells whose proliferation it is desired to inhibit. In certain embodiments, expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the HIN-1 polypeptide or functional fragment of interest with an initiator methionine and optionally a targeting sequence is operatively linked to a promoter or enhancer-promoter combination.

Short amino acid sequences can act as signals to direct proteins to specific intracellular compartments. Such signal sequences are described in detail in U.S. Pat. No. 5,827,516, incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

One alternative in vivo approach involves administering to a subject (e.g., a breast or lung tumor patient) having cancer cells in which the HIN-1 gene is low and/or a HIN-1 promoter region is methylated a compound that reduces methylation of the HIN-1 promoter region. One such compound is 5-aza-2'-deoxycytidine. Another approach involves administration of histone deacetylase inhibitors (e.g., trichostatin or sodium butyrate) which induce expression of methylated genes. Such compounds could induce expression of HIN-1 in cells (e.g., breast cancer cells) that either express it poorly or do not express it at all. Doses, frequency of doses, and routes of administration of methylation and histone deacetylase inhibitors will be as described above for HIN-1 polypeptides and functional fragments thereof. Human patients can be treated by, for example, one or more (e.g., two, three, four, five, six, seven eight, nine, or ten) intravenous infusions of 5-aza-2'-deoxycytidine (100-1,000 mg/m$^2$)

Ex Vivo Approaches

An ex vivo strategy can involve transfecting or transducing cells obtained from the subject with a polynucleotide encoding an HIN-1 polypeptide or functional fragment-encoding nucleic acid sequences described above. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the HIN-1 polypeptide or functional fragment for as long as they survive in the subject. Alternatively, tumor cells, preferably obtained from the subject but potentially from an individual other than the subject, can be transfected or transformed by a vector encoding a HIN-1 polypeptide or functional fragment thereof. The tumor cells, preferably treated with an agent (e.g., ionizing irradiation) that ablates their proliferative capacity, are then introduced into the patient, where they secrete exogenous HIN-1.

The ex vivo methods include the steps of harvesting cells from a subject, culturing the cells, transducing them with an expression vector, and maintaining the cells under conditions suitable for expression of the HIN-1 polypeptide or functional fragment. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the coding sequence or of a drug resistance gene. The cells may then be lethally irradiated (if desired) and injected or implanted into the patient.

Methods of Screening for Compounds that Enhance the Ability of HIN-1 to Inhibit Proliferation of Cancer Cells.

The invention provides methods for identifying compounds (small molecules or macromolecules) that enhance the ability of HIN-1 to inhibit proliferation of cancer cells. Such a method can involve, e.g., culturing a HIN-1 polypeptide of the invention (or a functional fragment thereof) with cancer cells in the presence of a test compound. Cancer cells can be any of those disclosed herein. Useful HIN-1 polypeptides include those with amino acid sequences identical to wild-type sequences or they can contain one or more (e.g., one, two, three, four, five, six, seven, eight, nine, 10, 12, 14, 17, 20, 25, 30, 35, 40, 50, 60, 70, 80, 90, 100 or more) conservative substitutions. The HIN-1 polypeptide can be natural or recombinant. Compounds that enhance the inhibition by the HIN-1 polypeptide of proliferation of the cancer cells will likely be compounds that inhibit tumor growth.

A candidate compound whose presence requires at least 1.5 fold (e.g., 2-fold, 4-fold, 6-fold, 10-fold, 100-fold, 1000-fold, 10,000 fold, or 100,000-fold) less HIN-1 to achieve a defined arbitrary level of inhibition of cancer cell proliferation than achieved in the absence of the compound can be useful for enhancing inhibition of cancer cell proliferation, and thus can be useful as a cancer therapeutic agent.

The invention also relates to using HIN-1 or functional fragments thereof to screen for compounds that can interact with HIN-1 and potentially thereby enhance its ability to inhibit the proliferation of cancer cells. One of skill in the art would know how to use standard molecular modeling or other techniques to identify small molecules that would bind to appropriate sites (e.g., allosteric sites) on HIN-1. One such example is provided in Broughton (1997) Curr. Opin. Chem. Biol. 1, 392-398.

The invention also features a method of identifying a compound (small molecule or macromolecule) that can replace the function of HIN-1 in a cell that does not express HIN-1. The method involves exposing both (1) cells not expressing HIN-1 and (2) cells expressing HIN-1 to a test compound and determining whether the compound inhibits (i.e., totally abrogates or diminishes in part) the proliferation of either type of cells. Any compound that decreases the proliferation of cells not expressing HIN-1 but either does not inhibit the proliferation of cells expressing HIN-1 or inhibits the proliferation of cells expressing HIN-1 to a lesser degree (e.g., 20%, 30%, 40%, 50%, 60%, 70%, 80%, 90%, 95%, 97%, 98%, or 99% less) than it does the proliferation of cells not expressing HIN-1, is potentially a compound that replaces the function of HIN-1 in cells not expressing HIN-1. The cells expressing the HIN-1 can be any of the cells disclosed herein as expressing HIN-1 (e.g., normal breast epithelial cells or certain breast cancer cells). The cells can express HIN-1 from endogenous HIN-1 genes or they can be recombinant cells expressing, for example, a gene either stably or transiently transfected into the cells. The cells not expressing HIN-1 can be any cells that naturally (e.g., because of mutation or endogenous regulatory mechanisms) lack expression of HIN-1, e.g., many breast cancer cell lines or any of a variety of normal or tumor cells disclosed herein. The cells can also be those in which lack of HIN-1 expression is artificially induced, e.g., by gene "knockout" technology, antisense methodologies, ribozyme, or RNAi methodologies. All these techniques are familiar to those in the art. The cells lacking expression of HIN-1 and those expressing HIN-1 will preferably be of the same histological type. Treatment of the cells with the test compound can be carried out by culturing the cells with the test compound and measuring their level of proliferation. Alternatively, the cells can be exposed to the test compound for a period of time (e.g., one minute, 10 minutes, 30 minutes, one hour, two hours, four hours, eight hours, 12 hours, 18 hours, 24 hours, two days, three days, 1 week, two weeks, 1 month, 2 months, three months or longer), after which the test compound is removed, and the cells are cultured for an additional period of time (e.g., one minute, 10 minutes, 30 minutes, one hour, two hours, four hours, eight hours, 12 hours, 18 hours, 24 hours, two days, three days, 1 week, two weeks, 1 month, 2 months, three months or longer) and their proliferation is measured. Methods of determining relative levels of cell proliferation are known in the art, e.g., measurement of [$^3$H]-thymidine incorporation into the DNA of the cells or cell counting using, optionally, a vital stain or a dye that is excluded by viable cells, e.g., trypan blue or eosin.

HIN-1 Antibodies

The invention features antibodies that bind to either or both of the HIN-1 polypeptides or fragments of such polypeptides. Such antibodies can be polyclonal antibodies present in the serum or plasma of animals (e.g., mice, rabbits, rats, guinea pigs, sheep, horses, goats, cows, or pigs) which have been immunized with the relevant HIN-1 polypeptide or peptide fragment using methods, and optionally adjuvants, known in the art. Such polyclonal antibodies can be isolated from serum or plasma by methods known in the art. Monoclonal antibodies that bind to the above polypeptides or fragments are also encompassed by the invention. Methods of making and screening monoclonal antibodies are well known in the art.

Once the desired antibody-producing hybridoma has been selected and cloned, the resultant antibody can be produced by a number of methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for HIN-1, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) *Science* 240, 1041-43; Liu et al. (1987) *J. Immunol.* 139, 3521-26; Sun et al. (1987) *PNAS* 84, 214-18; Nishimura et al. (1987) *Canc. Res.* 47, 999-1005; Wood et al. (1985) *Nature* 314, 446-49; Shaw et al. (1988) *J. Natl. Cancer Inst.* 80, 1553-59; Morrison, (1985) *Science* 229, 1202-07; Oi et al. (1986) *BioTechniques* 4, 214; Winter, U.S. Pat. No. 5,225,539; Jones et al. (1986) *Nature* 321, 552-25; Veroeyan et al. (1988) *Science* 239, 1534; and Beidler et al. (1988) *J. Immunol.* 141, 4053-60.

Also included within the scope of the invention are antibody fragments and derivatives which contain at least the functional portion of the antigen binding domain of an antibody that binds specifically to HIN-1. Antibody fragments that contain the binding domain of the molecule can be generated by known techniques. For example, such fragments include, but are not limited to: $F(ab')_2$ fragments which can be produced by pepsin digestion of antibody molecules; Fab fragments which can be generated by reducing the disulfide bridges of $F(ab')_2$ fragments; and Fab fragments which can be generated by treating antibody molecules with papain and a reducing agent. See, e.g., National Institutes of Health, 1 *Current Protocols In Immunology*, Coligan et al., ed. 2.8, 2.10 (Wiley Interscience, 1991). Antibody fragments also include Fv (e.g., single chain Fv (scFv)) fragments, i.e., antibody products in which there are few or no constant region amino acid residues. An ScFv fragment is a single polypeptide chain that includes both the heavy and light chain variable regions of the antibody from which the ScFv is derived. Such fragments can be produced, for example, as described in U.S. Pat. No. 4,642,334, which is incorporated herein by reference in its entirety.

Methods of Diagnosis

The invention also features diagnostic assays. Such assays are based on the findings that: (a) the hHIN-1 gene is either not expressed or is poorly expressed in a majority of breast and lung cancer cells while it is highly expressed in normal breast and lung tumors; and (b) many or most C residues in CpG sequences in a CpG island of the 5' promoter region of the hHIN-1 gene are methylated in the majority of breast tumors while none or very few of such residues are methylated in normal breast tissue. Thus, findings of either (a) no or low expression of the HIN-1 gene in test cells; or (b) methylation of many or most C residues in CpG sequences in a CpG island of the 5' promoter region of the hHIN-1 gene in test cells, would indicate that the test cells are cancer cells. Such tests can be used on their own or, preferably, in conjunction with other procedures to test for cancer in appropriate subjects, e.g., human breast cancer patients. Test cells can be any cells with the potential to become or be any of the cancer cells listed herein. Thus, they can be, for example, breast cells, lung cells, prostate cells, pancreatic cells, gastrointestinal (e.g., colon) cells, or skin cells (e.g., melanocytes).

The level of expression of HIN-1 genes in test cells can measured by any of a variety of methods known in the art. In general, such methods measure the level of either HIN-1 mRNA or HIN-1 polypeptide in test cells. In order to measure mRNA levels, test cells can be lysed and the levels of HIN-1 mRNA in the lysates or in RNA purified or semi-purified from the lysates determined by any of a variety of methods familiar to those in the art. Such methods include, without limitation, hybridization assays using detectably labeled HIN-1 specific DNA or RNA probes (see Example 3) and quantitative or semi-quantitative RT-PCR methodologies using appropriate HIN-1 gene-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantitating mRNA include the RNA protection assay (RPA) and SAGE.

Methods of measuring protein levels in test cells are known in the art. Many such methods employ antibodies (e.g., monoclonal or polyclonal antibodies) that bind specifically to the HIN-1 polypeptide. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to lysates of test cells and others (e.g., immunohistological methods or fluorescence flow cytometry) to histological sections or unlysed cell suspensions. Methods of measuring the amount of label will be depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase or horseradish peroxidase), fluorescent moieties (e.g., fluorescein, rhodamine, or phycoerythrin), or luminescent moieties (e.g., Qdot™ nanoparticles supplied by the Quantum Dot Corporation, Palo Alto, Calif.). Other applicable assays include quantitative immunoprecipitation or complement fixation assays.

Generally, the level of HIN-1 mRNA or protein in cancer cells will be at least two-fold (e.g., three-fold, four-fold, five-fold, six-fold, seven-fold, eight-fold, 10-fold, 15-fold, 20-fold, 40-fold, 60-fold, 80-fold, 100-fold, 500-fold, 1,000-fold, or higher-fold) less than in the normal cell counterpart of the cancer cell.

Methods of measuring the number of methylated C residues in the CpG sequences within the CpG island of the HIN-1 promoter are known in the art. One such methodology is described in Example 4. In FIG. 8 is shown the nucleotide sequence (SEQ ID NO:19) of DNA that, in the hHIN-gene, lies immediately 5' of the ATG initiation codon of the hHIN-1 coding region and that includes the CpG island referred to above. While the residue designated "N" in SEQ ID NO19 (FIG. 8) has not been identified, it is either a "C" or a "G". All or part of the SEQ ID NO:19 can be used in these assays.

Furthermore, C residues within CpG sequences at the 5' end of the HIN-1 coding region can be included in such assays.

Standardizing such methylation assays to discriminate between cancer and non-cancer cells of interest would involve experimentation familiar to those in the art. For example, the methylation status of the HIN-1 promoter region in DNA from sample cancer cells of interest obtained from a large number of patients can be compared to the methylation status of the HIN-1 promoter region in DNA from normal cells corresponding to the cancer cells obtained either from the same patients or from normal individuals. From such experimentation it will be possible to establish a range of "cancer levels" of methylation and a range of "normal levels" of methylation. Alternatively, the methylation status of the HIN-1 promoter region in DNA from cancer cells of each patient can be compared to the methylation status of the HIN-1 promoter region in DNA from normal cells (corresponding to the cancer cells) obtained from the same patient. In such assays, it is possible that methylation of as few as one cytosine residue could discriminate between cancer and non-cancer cells.

Other methods for quantitating methylation of DNA are known in the art. Such methods are based on: (a) the inability of methylation-sensitive restriction enzymes to cleave sequences that contain one or more methylated CpG sites [Issa et al. (1994) *Nat. Genet.* 7:536-540; Singer-Sam et al. (1990) *Mol. Cell. Biol.* 10:4987-4989; Razin et al. (1991) *Microbiol. Rev.* 55:451-458; Stoger et al. (1993) *Cell* 73:61-71]; and (b) the ability of bisulfite to convert cytosine to uracil and the lack of this ability of bisulfite on methylated cytosine [Frommer et al. (1992) *Proc. Natl. Acad. Sci. USA* 89:1827-1831; Myöhänen et al. (1994) *DNA Sequence* 5:1-8; Herman et al. (1996) *Proc. Natl. Acad. Sci. USA* 93:9821-9826; Gonzalgo et al. (1997) *Nucleic Acids Res.* 25:2529-2531; Sadri et al. (1996) *Nucleic Acids Res.* 24:5058-5059; Xiong et al. (1997) *Nucleic Acids Res.* 25:2532-2534].

The following examples are meant to illustrate, not limit, the invention.

EXAMPLES

Example 1

Materials and Methods

Purification of luminal mammary epithelial cells. The presence of normal and DCIS mammary epithelium in breast tissue samples was confirmed by examination of hematoxylin-eosin stained frozen sections. Breast tissue was minced into small pieces and digested in DMEM/F12 medium (Life Technologies, Rockville, Md.) supplemented with 1% fetal bovine serum (FBS) and 2 mg/ml collagenase I (Sigma; Catalog No. C0130) and 2 mg/ml hyaluronidase (Sigma; Catalog No. H3506) at 37° C. for 2 hours with constant agitation. Cells were collected by centrifugation (3,000 rpm for 10 min.), washed in 10 ml of PBS (phosphate buffered saline, Life Technologies), centrifuged again, and treated with trypsin (5 ml 0.05% of Trypsin-EDTA; Life Technologies) at 37° C. for 5 min. Cells were collected by centrifugation and resuspended in 200 µl of PBE (PBS, 1% bovine serum albumin, 2 mM EDTA). Cells were purified using anti-BerEP4 antibody coated magnetic beads (Dynabeads™; 10 µl/~1 million cells) (Epithelial Enrich; Dynal, Oslo, Norway). The antibody coated magnetic beads were added to 200 µl of the cell suspension containing approximately $10^6$ cells. The mixture was incubated on ice for 10-30 min The beads with appropriate cells bound were pelleted by placing the bottom of the tube containing the mixture on a magnet. PBE containing cells not bound to beads was removed and the beads were resuspended in 200 µl PBE. This washing procedure was performed 3 times. After the last wash, cells bound to the beads (Dynabeads™) were lysed in RNA lysis buffer (mRNA Direct Kit, Dynal) and RNA was isolated according to the manufacturer of the mRNA Direct Kit mRNA isolation kit (Dynal).

Generation and analysis of SAGE libraries. SAGE libraries were generated following a modified micro-SAGE protocol, but including a 1% sodium dodecyl sulfate (SDS) washing/heating step following each enzymatic reaction in order to ensure complete inactivation of the enzymes. [Velculescu et al. (1995) *Science* 270, 484-487; Polyak et al. (1997) *Nature* 389, 300-305; Lal et al. (1999) *Cancer Res.* 59, 5403-5607; Velculescu et al. (1999) *Nature Genetics* 23, 387-388].

Cell lines and tissue. BT-20, BT-474, BT-549, Hs578T, MCF-7, MDA-MB-231, MDA-MB-468, MDA-MB-435S, SK-BR-3, T47D, UACC-812, UACC-893, and ZR-75-1 breast cancer cell lines were obtained from the American Type Culture Collection (ATCC; Manassas, Va.). SUM-44, SUM-52, SUM-102, SUM149, SUM-159, SUM-185, SUM-190, SUM-225, SUM-229, and SUM-1315 cell lines were a generous gift of Dr. Steve Ethier (University of Michigan Medical Center). The HCC1937 BRCA1 minus cell line was obtained from Dr. Gail Tomlinson (University of Texas Southwestern Medical Center). The 21MT1, 21MT2, 21NT, and 21PT cell lines were obtained from Dr. Arthur Pardee (Dana-Farber Cancer Institute). Cells were grown in media recommended by the ATCC or by the establishing investigators. However, 48 hours prior to RNA extraction, all cell lines were switched to DMEM/F12 medium supplemented with 5% FBS in order to minimize gene expression differences due to culture conditions. To test the effect of methyl transferase inhibitors, cells were grown in the presence of 25 µM 5-aza-2'-deoxycytidine for 10 days, then harvested for RNA preparation. Primary tumors were obtained from consecutive surgeries from the Brigham and Women's Hospital and Massachusetts General Hospital, snap frozen on dry ice, and stored at −80° C. until use. Primary mammary epithelial cell cultures were initiated with cells purified from organoids as described above for the purification of luminal mammary epithelial cells and the cells were grown in MBEM medium (Clonetics, Walkersville, Md.). Laser capture microdissection (LCM) of frozen tumors was performed essentially as described. [Sgroi et al. (1999) *Cancer Res.* 59:5656-5661].

Primary cultures of human bronchial epithelial cells were purchased from Clonetics (Walkersville, Md.) and were cultured in the presence or absence of 1 mM all-trans retinoic acid essentially as previously described [Koo et al. (1999) *Am. J. Respir. Cell Mol. Biol.* 20:43-52].

Mouse organs and embryos were collected following protocols approved by the Animal Care and Use Committee of the Dana-Farber Cancer Institute.

RNA preparation and Northern blot analysis. RNA isolation, RT-PCR and Northern blot analysis were performed essentially as described [Polyak et al. (1997)]. Human multiple tissue northern blots and expression arrays were purchased from Clontech (Palo Alto, Calif.) and hybridized with a PCR-derived, full-length HIN-1 cDNA probe according to the manufacturer's instructions.

mRNA in situ hybridization. Digitonin-labeled mouse HIN-1 riboprobes were generated and mRNA in situ hybridization was performed as described by Qian et al. [(2001) *Genes Dev.* 15:2533-2545].

hHIN-1 methylation, loss of heterozygocity and mutation analysis. Searching the draft of the human genome sequence with the hHIN-1 cDNA sequence identified a genomic clone (CTB-36B8) containing the entire hHIN-1 gene, the proximal promoter region of which contained an apparent CpG island. To determine the location of methylated cytosines, genomic DNA was extracted from the cells, bisulfite treated and purified as previously described [Herman et al. (1998) *Proc. Natl. Acad. Sci. USA* 95:6870-6875]. PCR amplification was performed using the following primers designed to amplify the coding strand (nucleotides −345 to +72) of bisulfite treated DNA: forward primer-5'-gagggaaagttttttttatttgg-3' (SEQ ID NO:9) and reverse primer-5'-caaaactaacaaaacaaaacca-3' (SEQ ID NO:10). PCR reactions were performed in 50 µl reactions containing 16.6 mM $(NH_4)_2SO_4$, 67 mM Tris pH8.8, 6.7 mM $MgCl_2$, 10 mM β-mercaptoethanol, 1.5 mM each deoxynucleotide, 35 ng of each primer, 1 µl of Platinum® Taq (Life Technologies) and 2 of bisulfite treated genomic DNA as template. Amplifications were performed using a "touch-down" protocol: initial denaturation 95° C. 3 min., 5 cycles of 95° C. 30 sec., 61° C. 1 min, 70° C. 1 min.; 35 cycles of 95° C. 30 sec., 57° C. 1 min, 70° C. 1 min.; followed by 70° C. 5 min. PCR products were subcloned into the pZERO1.0™ plasmid (Invitrogen) and 4-6 independent colonies were sequenced for each PCR product. Based on the sequence of methylated/unmethylated templates, PCR primers were designed for the specific amplification of methylated or unmethylated DNA. After several tests, the following primers were found to be highly specific and used in all subsequent experiments: methylated DNA forward primers F1 (nt −209 to −186): 5'-gttaagaggaagttttcgaggttc-3' (SEQ ID NO:11), F2 (nt −172 to −149): 5'-ggtacgggtttttacggttcgtc-3' (SEQ ID NO:12), reverse primer R2 (nt −37 to −58): 5'-aact-tcttatacccgatcctcg-3' (SEQ ID NO:13); unmethylated DNA forward primers F1 (nt −209 to −186): 5'-gttaagag-gaagttttgaggttt-3' (SEQ ID NO:14), F2 (nt −172 to −149): 5'-ggtatgggtttttatggtttgtt-3' (SEQ ID NO:15), reverse primer R2 (nt −37 to −58): 5'-caaaacttatatacccaatcctca-3' (SEQ ID NO:16). PCR amplifications were performed as described above; PCR fragments were analyzed on 3% agarose gels.

For loss of heterozygocity studies, PCR forward (5'-tttc-cctgcttccacactagc-3') (SEQ ID NO:17) and reverse (5'-agat-taagaaggaattgacct-3') (SEQ ID NO:18) primers were designed to amplify a CA repeat present in the CTB-36B8 genomic clone containing the hHIN-1 gene. PCR amplifications using $^{32}P$ end-labeled primers were performed essentially as described [Thiagalingam et al. (1996) *Nat. Genet.* 13(3):343-346]. Mutation screen was performed either on PCR-derived, full-length cDNA fragments or PCR fragments of individual exons amplified from genomic DNA using intron specific primers.

Generation of recombinant hHIN-1 protein and polyclonal anti-HIN-1 antibodies. Human HIN-1 encoding cDNA without the start methionine codon was PCR amplified and subcloned into the pQE-30 expression vector (QIAexpress® Protein Purification System; Qiagen, Valencia, Calif.) in frame with an N-terminal hexahistidine tag and transformed into MJ15[pREP4] bacteria. For large scale protein purification, a single bacterial colony was inoculated into 20 ml of TB (Terrific Broth; Life Technologies) medium containing 200 µg/ml ampicillin and 25 µg/ml kanamycin, grown overnight at 37° C., and transferred into 1000 ml of the same medium the following morning. Once the $OD_{600}$ of the culture had reached 0.6-0.8, protein expression was induced at by the addition of isopropyl-β-D-thiogalactopyranoside (IPTG; 1 mM final concentration) to the medium followed by incubation for an additional four hours. Bacteria were collected by centrifugation and lysed by sonication in 50 ml of lysis buffer containing 8 M urea, 50 mM Tris (pH 7.7), 20 mM imidazole, 1 M NaCl, 0.1% Triton X-100, 10 mM β-mercaptoethanol, and 20% ethanol. Cleared cell lysates were then incubated with 0.5 ml of Ni-NTA Agarose (Qiagen) for one hour at room temperature, followed by repeated washes with lysis buffer. Bound proteins were then eluted in a buffer containing 300 mM imidazole, 0.5 M NaCl, 50 mM Tris (pH), and 10% glycerol and dialyzed into PBS containing 10% glycerol at 4° C. prior to use.

Rabbit polyclonal antibody specific for hHIN-1 protein was prepared by Zymed (South San Francisco, Calif.).

Generation of hHIN-1 mammalian expression constructs and recombinant adenoviruses. For stable constitutive expression in mammalian cells, hHIN-1 encoding cDNA (or p53 encoding cDNA) was PCR amplified and subcloned into the pCEP4 vector (Invitrogen, Carlsbad, Calif.). For the generation of a recombinant adenovirus the hHIN-1 cDNA was PCR amplified and subcloned into the Kpn I-Xho I site of the pAd-Track-CMV adenoviral vector followed by recombination and adenovirus generation using the Ad-Easy™(Quantum Biotechnologies, Montreal, Canada) system [He et al. (1998) *Proc. Natl. Acad. Sci. USA* 95:2509-2514]. Expression of hHIN-1 protein was confirmed by western blot analysis using anti-hHIN-1 polyclonal antibodies.

Colony assays, cell cycle analysis and western blot analysis. For colony assay experiments, cells in 100 mm plates were transfected with a mix of 42 µl of FuGene6 (Roche) and 21 µg of the indicated plasmid. 24 hours after transfection, 84% of the cells were plated into 2 T25 tissue culture flasks in medium without a selection drug. Twenty-four hours later the medium was replaced with selection medium containing hygromycin. Colonies were allowed to grow for 2 weeks after which they were visualized by crystal violet staining.

For cell cycle analyses, cells were plated into 6 well tissue culture plates ($1 \times 10^5$ cells/well) and infected with 2 µl (~50-100 m.o.i. (multiplicity of infection)) of Ad-Track-GFP (Green Fluorescence Protein) or Ad-Track-Histag-HIN-1 replication defective recombinant adenoviruses. For some of these experiments cells were grown in medium containing 0.2% serum in order to maximize a potential growth inhibitory effect. For western blot analysis, cells and media from 293 cells transfected with pCEP4 (control vector containing no expressible cDNA insert), pCEP4-Histag-HIN-1 (vector containing cDNA encoding hHIN-1 fused to hexahistidine) constructs, and MCF10A or SUM159 cells infected with Ad-Track-GFP or Ad-Track-Histag-HIN-1 were lysed in denaturing urea buffer (as described for purification of recombinant hHIN-1 from bacteria) and the lysates were incubated with Ni-NTA beads. Proteins bound to the beads were eluted off the beads, subjected to SDS-PAGE, and immunoblotted with rabbit polyclonal antibody specific for hHIN-1 diluted 1:1,000.

Example 2

Generation and Analysis of SAGE Libraries

SAGE libraries were generated from two independent cases of DCIS and two samples of luminal mammary epithelium and analyzed. One of the DCIS tumors was a high grade, comedo DCIS (DCIS1), while the other one was a solid, intermediate-grade DCIS (DCIS2). Normal luminal mammary epithelial cells were derived from corresponding contralateral prophylactic mastectomy tissue (Normal 2) obtained from the DCIS2 case or from breast reduction surgery on an unrelated patient (Normal 1). Luminal mammary epithelial cells and breast cancer cells were purified using anti-Ber-EP4 coated magnetic beads, and SAGE libraries were generated using a modified version of a micro-SAGE protocol.

From the four SAGE libraries 160,046 tags were obtained, approximately 40,000 from each library. With this high number of tags, it was possible to compare the expression levels of close to 30,000 unique transcripts. Pair-wise comparison of these SAGE libraries identified several differentially expressed tags. 97 tags were elevated at least 10-fold in one or the other DCIS library, while 132 tags were at least 10-fold more abundant in the normal libraries. Interestingly there was only 1 tag that was highly elevated (about 113 to 95-fold) and there were 9 tags that were 10-fold decreased in both DCIS libraries. These 10 tags were searched against ~85 other SAGE libraries derived from a variety of normal and cancerous tissue types. One of the tags was particularly interesting, since it was present only in the two normal luminal mammary epithelial cell SAGE libraries. This finding indicated that the tag was derived from a transcript from which a polypeptide associated with mammary epithelium specific function is translated. Database searches identified a 461 by human full-length Unigene cDNA clone corresponding to this tag. The full length cDNA (461 bp) is predicted to include a coding sequence (SEQ ID NO:3) (FIG. 1A) encoding a small protein (the hHIN-1 polypeptide) of 104 amino acids (~11 kDa) (SEQ ID NO:1) (FIG. 2A). This conclusion was confirmed by in vitro transcription/translation experiments. The protein was designated human HIN-1 (hHIN-1). The hHIN-1 protein contains a putative signal peptide (see above), and is predicted to be secreted. This consideration and the fact that the gene product regulates cell proliferation (see below) indicates that hHIN-1 is a novel cytokine. A database search (dbest tblastx) also identified a homologous mouse cDNA sequence (SEQ ID NO:7) (FIG. 3A) encoding a polypeptide (mHIN-1; SEQ ID NO:5) (FIG. 4A) of the same length as the hHIN-1 polypeptide and with an analogous signal peptide. Due to its homology to hHIN-1 (60.8% identity at the amino acid level), it is likely that mHIN-1 has essentially the same function as hHIN-1. The same database search revealed a rat partial cDNA sequence (SEQ ID NO:20) (FIG. 9A) encoding a polypeptide (SEQ ID NO:21) highly homologous to both hHIN-1 and mHIN-1. The rat polypeptide is 62% identical to the hHIN-1 polypeptide and is 84% identical to the mHIN-1 polypeptide. It seems likely that this amino acid sequence (SEQ ID NO:21) is rat HIN-1 (rHIN-1) missing several N-terminal amino acids and that, like mHIN-1, rHIN-1 has the same function as hHIN-1. In FIG. 10 is shown the amino acid sequences of hHIN-1, mHIN-1, and the partial sequence of rHIN-1 aligned for maximum homology. Amino acids indicated below the aligned sequences are those that are common to at least two of the polypeptides at the relevant positions.

Example 3 hHIN-1 Expression in Normal Tissues and in Breast Carcinomas

Figure 5B:
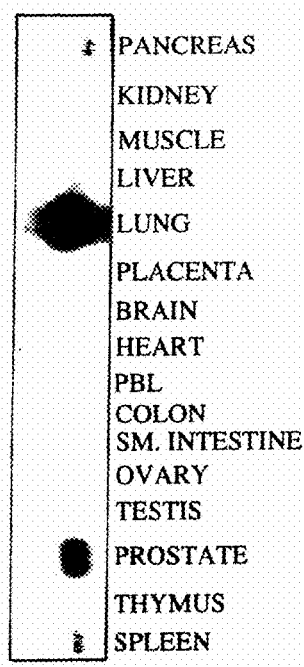
FIG. 5B is a photograph of an autoradiogram obtained from multiple tissue northern blots exposed to a $^{32}$P-labeled hHIN-1 cDNA probe.

The lack of SAGE tags corresponding to the hHIN-1 mRNA in 85 other SAGE libraries suggested an intriguing tissue specific pattern of hHIN-1 expression. To confirm this cell type-specific expression pattern, $^{32}$P-labeled hHIN-1 cDNA was hybridized to an expression array panel consisting of dots of mRNA from 76 human adult and fetal tissue types bound to a blotting membrane. In addition to mammary gland, the hHIN-1 gene appears to be highly expressed in lung, trachea, salivary gland, prostate, esophagus, duodenum, fetal lung and fetal kidney (FIG. 5A). Lower levels of hHIN-1 mRNA expression were detected in pancreas, pituitary gland, lymph node and accumbens nucleus. To verify the identity of the signal detected on the dot blots, multiple tissue northern blots were also exposed to $^{32}$P-labeled HIN-1 cDNA. The data confirmed that the hybridizing RNA corresponds to a single hHIN-1 mRNA (FIG. 5B). The high expression of hHIN-1 in tissues that contain epithelia-producing mesenchymal tissue suggest that HIN-1 might play a role in epithelial branching morphogenesis.

Figure 5C:
FIGS. 5C-5E are photomicrographs showing in situ hybridization (dark staining) of a digitonin labeled hHIN-1 anti-sense ribo-probe to normal mammary epithelium (20× magnification.
Figure 5D:
Figure 5E:
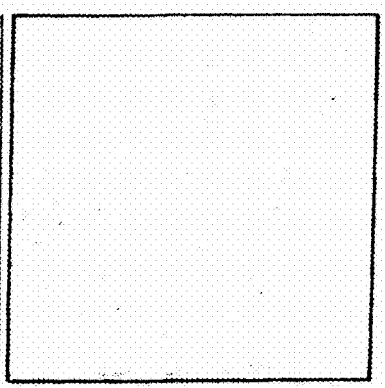
Figure 5F:
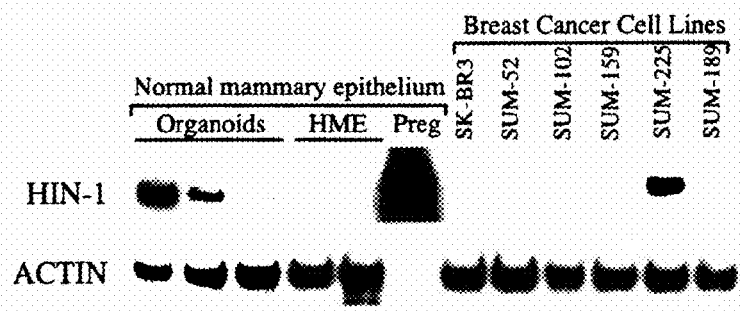
FIG. 5F is a photograph of an autoradiogram obtained from northern blots (exposed to a $^{32}$P-labeled hHIN-1 cDNA probe) of RNA isolated from: normal human mammary organoids ("organoids") of three individual patients; cultured primary human mammary epithelial cells ("HME"); mammary epithelial cells in a frozen section from a 25-week pregnant patient ("Preg"); and five breast cancer cell lines.
Figure 5G:
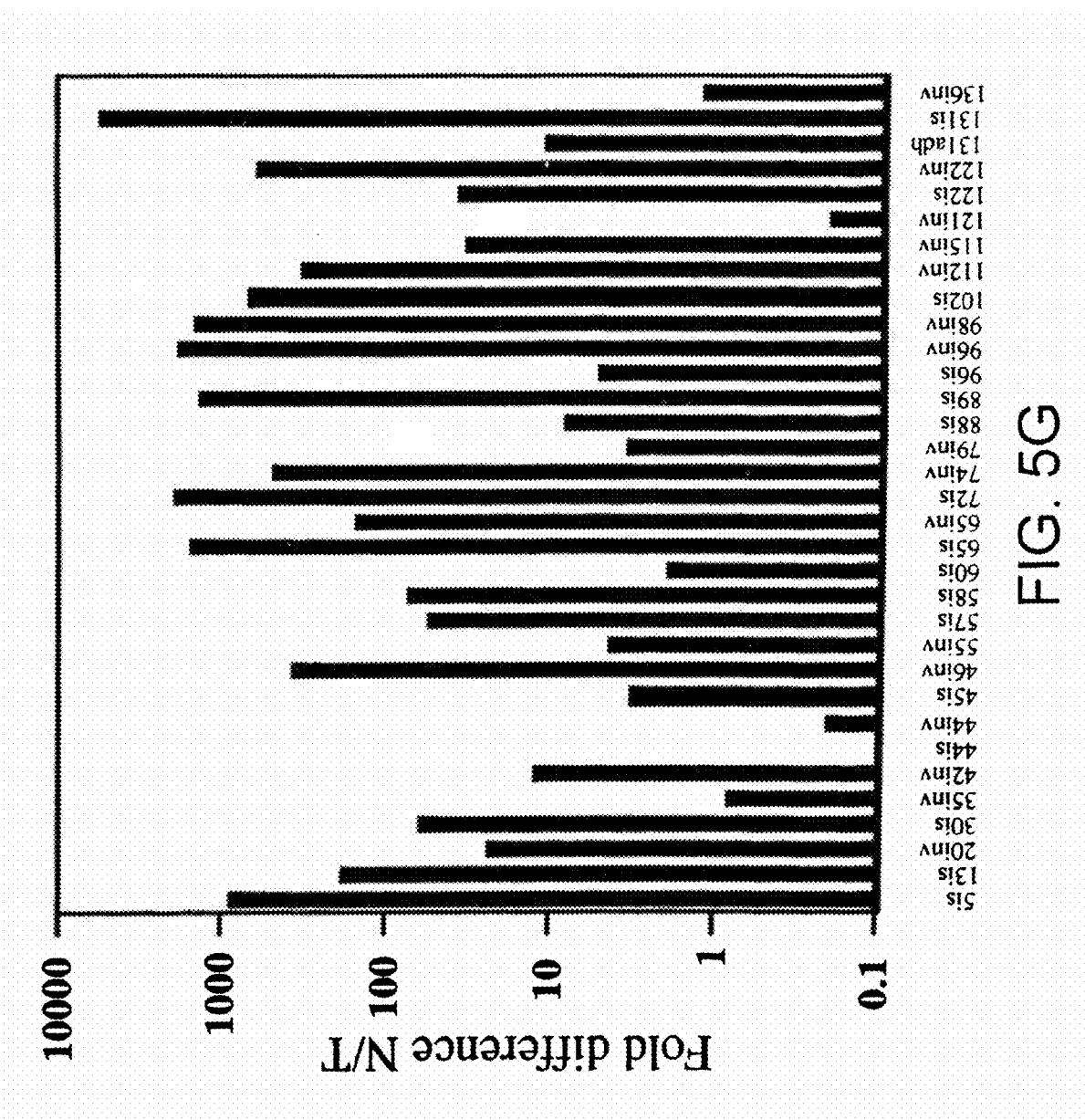
FIG. 5G is a bar graph showing the results of a real-time PCR analysis of hHIN-1 mRNA expression in laser capture microdissected breast cancer tissue.

SAGE analysis indicated hHIN-1 expression levels at least 20-fold lower in DCIS tissue than in two different normal luminal mammary epithelia. In situ hybridization was performed to confirm hHIN-1 expression at the cellular level. hHIN-1 is highly and specifically expressed in normal luminal epithelial cells of small ducts and lobules, but not that of large ducts (FIGS. 5C and 5D). In contrast, no hybridization signal was detected in DCIS (FIG. 5E). Northern blot analysis was performed to further evaluate hHIN-1 expression levels in multiple independent normal breast organoids, in primary mammary epithelial cell cultures and in breast cancer cell lines. A representative result of these experiments is shown in FIG. 5F. High levels of hHIN-1 expression were detected in freshly isolated breast organoids, but not in cultured normal mammary epithelial cells nor in most breast cancer cell lines tested by northern blot. Furthermore, we were unable to detect hHIN-1 mRNA by RT-PCR in 89% (25/28) of breast cancer cell lines. hHIN-1 expression was dramatically up-regulated in pregnant epithelium. The expression of hHIN-1 was further investigated by real-time PCR analysis of LCM dissected primary tumors. The results from 33 representative cases are shown in FIG. 5G. "Fold difference" indicates the ratio of hHIN-1 mRNA levels in normal versus cancerous epithelium isolated from the same patient. Only 4 tumors were found to express detectable hHIN-1 mRNA, while the majority of tumors (78%) had no detectable hHIN-1 expression. These primary tumors included in situ, invasive ductal and lobular carcinomas, and hHIN-1 expression was lost regardless of tumor stage and histological type. Thus, loss of hHIN-1 expression is an early and frequent event in human breast carcinomas. Interestingly, northern blot analysis of 40 primary lung tumors also revealed dramatically reduced (>90% compared to normal lung tissue) hHIN-1 mRNA levels.

Example 4 hHIN-1 Expression is Silenced by Methylation

The loss of hHIN-1 expression in the majority of breast cancers suggested a tumor suppressor function for hHIN-1. In order to evaluate if hHIN-1, following the Knudson model, undergoes biallelic inactivation in breast cancers, we performed LOH (loss of heterozygocity) and mutational analyses of the HIN-1 gene. A search of a draft of the human genome sequence using the sequence of hHIN-1 cDNA resulted in the identification of a genomic clone containing the entire hHIN-1 gene and an adjacent polymorphic CA repeat as being suitable for LOH analysis. Analysis of this CA repeat in 43 primary tumors revealed LOH in 25% of the informative cases. However, sequencing the other allele revealed no mutations. Similarly, PCR analysis of breast cancer cell lines detected no homozygous deletions, and sequence analysis of the hHIN-1 cDNA in four cell lines that expressed hHIN-1 revealed no mutations. Therefore, the loss of hHIN-1 expression in breast cancer is unlikely to be due to genetic events. It seemed likely that epigenetic mechanisms (such as DNA methylation) might instead be responsible.

This hypothesis was strengthened by the presence of a CpG island in the proximal promoter region of the hHIN-1 gene.

Figure 6A:
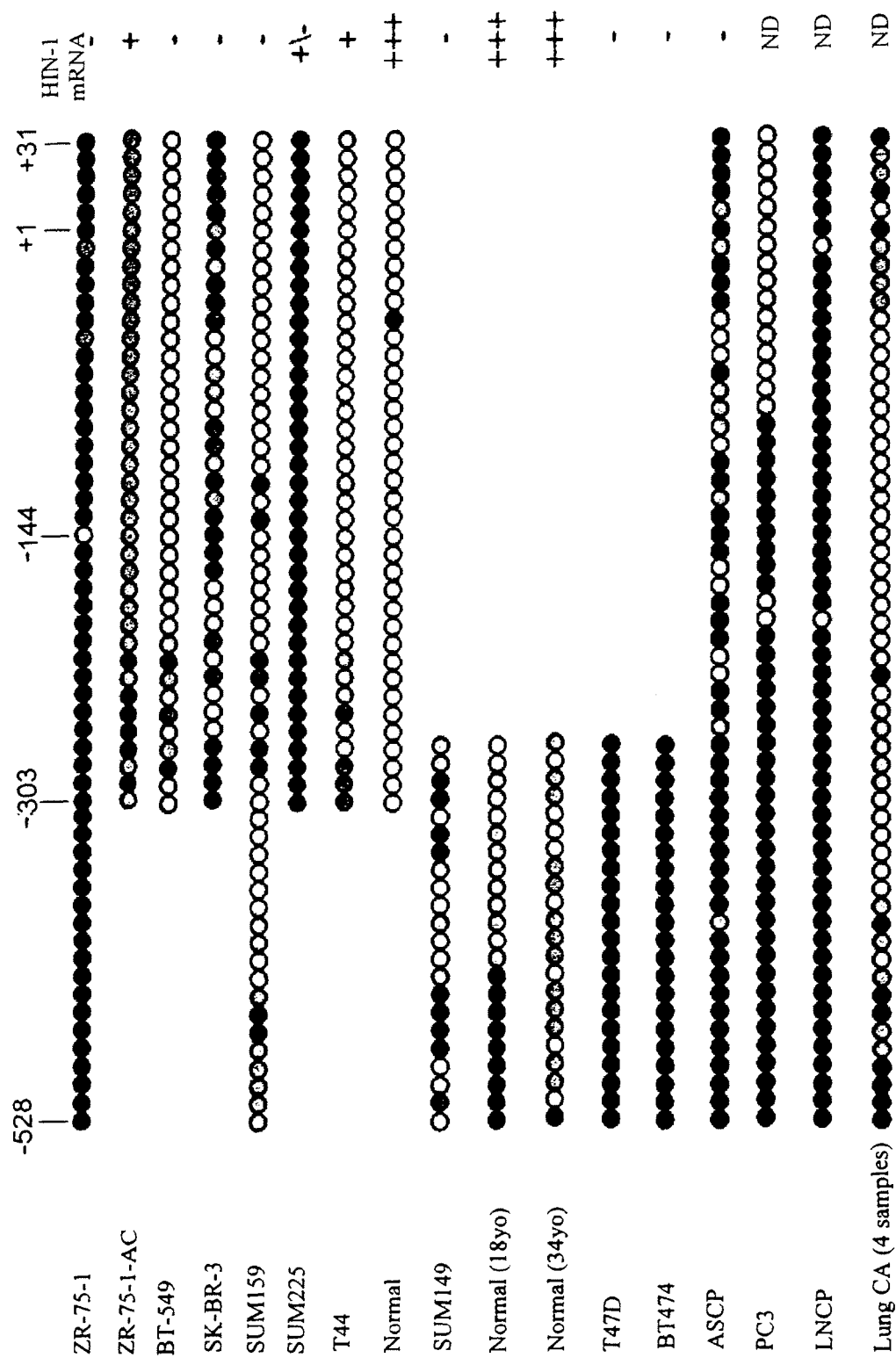
FIG. 6A is a diagram showing the results of a sequence analysis of bisulfite treated genomic DNA from the indicated cell lines. Each circle represents a potential methylation site and the intensity of circle-fill indicates the frequency at which the site was found to be methylated in the PCR product clones analyzed. The darkest fill represents 100%, no fill represents 0% and three intermediate intensities represent 75%, 50%, and 25%. Genomic DNA was extracted from ZR-75-1 cells ("ZR-75-1"), ZR-75-1 cells cultured with 5 aza-cytosine (5aza-C) ("ZR-75-1-AC"), BT-549 cells ("BT-549"), SK-BR-3 cells ("SK-BR-3") SUM159 cells ("SUM159"), SUM225 cells ("SUM225"), T44 cells ("T44"), normal mammary epithelial cells from three separate patients ("Normal"), normal mammary cells from an 18-year old patient ("Normal (18yo)"), normal mammary cells from a 34-year old patient ("Normal (34yo)"), T47D cells ("T47D"), BT474 cells ("BT474"), ASCP cells ("ASCP"), PC3 cells ("PC3"), LNCP cells ("LNCP"), and pooled lung cancer tissue from four individual patients ("Lung CA (4 samples)"), and analyzed. Also shown are relative levels of hHIN-1 mRNA in relevant cells and tissues. "+++" indicates high levels of hHIN-1 mRNA that were detectable by Northern blot analysis of 1 μg (or less) of total RNA (these levels were detected only in normal breast tissues). "+" indicates hHIN-1 mRNA levels detectable by Northern blot analysis of 5 μg of total RNA. "−" indicates hHIN-1 mRNA levels undetectable by Northern blot analysis. "+/−" for SUM225 cells is explained in Example 4.
Figures 6B, 6C, 7:
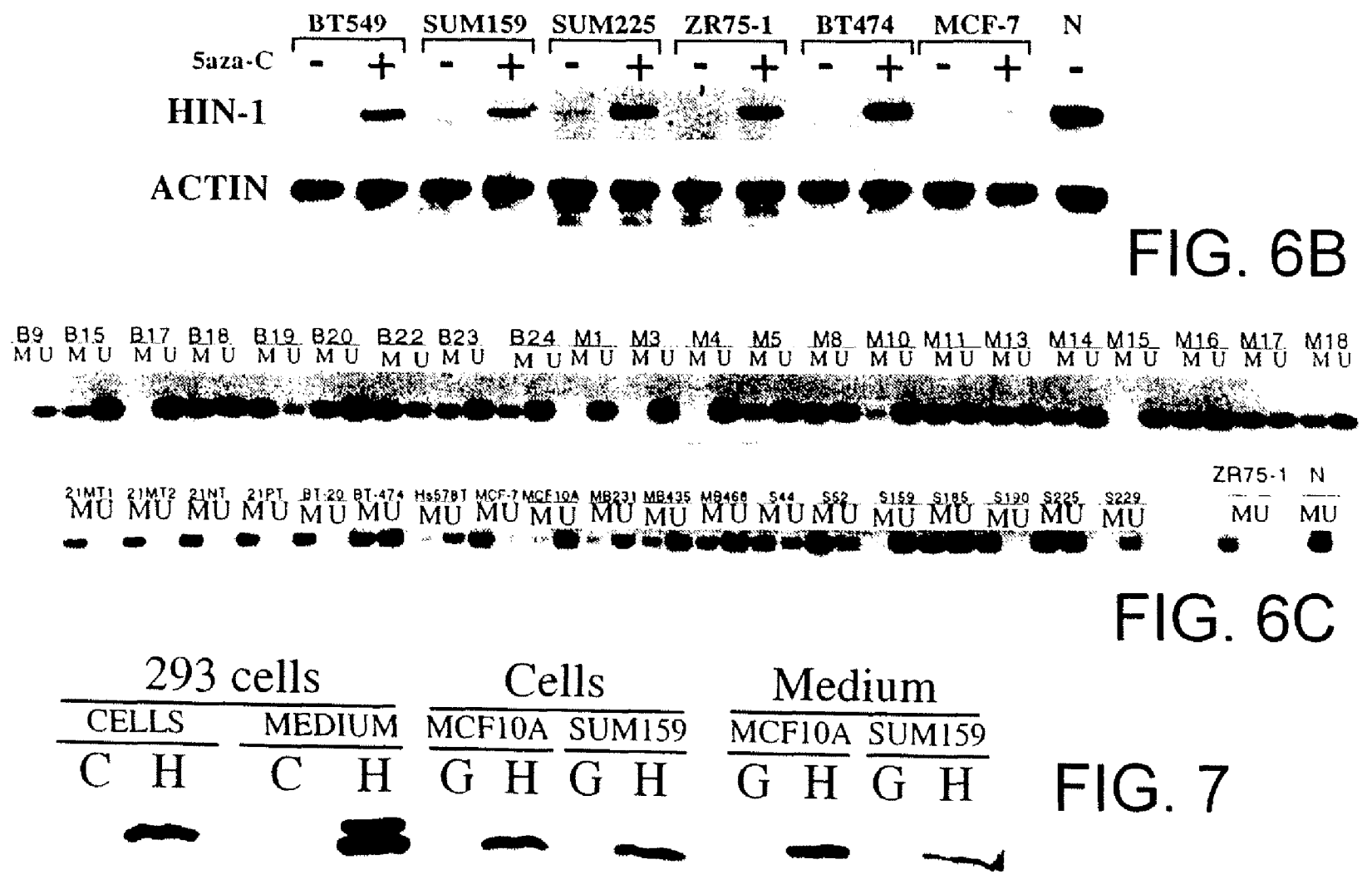

To investigate the potential role of DNA hypermethylation in silencing hHIN-1 expression, the sequence of its promoter region in bisulfite treated DNA isolated from normal mammary epithelial cells and human breast cancer cell lines was analyzed. FIG. 6A shows the frequency of methylation of up to 56 CpG sites in the hHIN-1 promoter regions in 4-10 individual PCR product clones derived from each cell line or tissue. Also shown in FIG. 6A are the relative levels of hHIN-1 mRNA in the relevant cells. In DNA from some cells, shorter regions ("−304 to +31" or "−532 to −281") were analyzed while in others a longer region ("−532 to +31") was analyzed. The "−532 to +31" region contained the sequence shown in FIG. 8 (SEQ ID NO:19) and the first 12 nucleotides of the hHIN-1 coding sequence. The "−304 to +31" region contained the 3' 323 nucleotides of SEQ ID NO:19 and the first 12 nucleotides of the hHIN-1 coding sequence. As shown in FIG. 6A, virtually all of the CpGs in the proximal promoter region analyzed are methylated in breast cancer cells with no hHIN-1 expression (ZR-75-1, T47D, and BT474), while essentially no methylated CpGs were found in normal mammary epithelial cell samples ("Normal"). The data shown for "Normal" were pooled from data obtained from separate analyses of DNA from each of three independent normal mammary epithelial cell samples. Normal breast tissue samples from an 18-year old and 34-year old patient ("Normal (18yo)" and "Normal (34yo)", respectively) were also analyzed. The analysis of the tissue from the 34 year old patient indicated a high level of hHIN-1 mRNA in the tissue and a low level of methylation of the hHIN-1 promoter region. The analysis of the tissue from the 18-year old patient also indicated a high level of mRNA in the tissue but with significant methylation of at least the distal end of the hHIN-1 promoter region. It is possible that hHIN-1 gene expression is affected more potently by methylation of CpG sites more proximal to the transcription initiation site than by methylation of CpG sites more distal to the transcription initiation site. Alternatively, or in addition, there may be age-dependent differences in methylation of the HIN-1 gene; such age-dependent differences in methylation have been observed in other genes. Interestingly, some breast cancer cell lines (BT-549, SK-BR-3, SUM159 and SUM149) and parts of one tumor (T44) had some expression of hHIN-1 mRNA, although at much lower levels than that of normal cells (and detectable by RT-PCR but not by Northern blot analysis), and their promoter regions were found to be partially methylated (FIG. 6B). The SUM225 breast cancer cell line initially had hHIN-1 mRNA levels comparable to that of normal mammary epithelium (FIG. 5C); however, it progressively lost hHIN-1 expression in later passages (FIG. 6B) and its promoter region became highly methylated (FIG. 6A). In a pancreatic cancer cell line (ASCP) no hHIN-1 mRNA was detected and a high degree of methylation of the hHIN-1 promoter region was observed. In addition, a high degree of methylation of the hHIN-1 promoter region was found in two prostate cancer cell lines (PC3 and LNCP). A moderate level of the hHIN-1 promoter methylation was detected in DNA from a pool of four lung carcinoma tissue samples ("Lung CA"). Thus, there appears to be a strong correlation between hHIN-1 promoter region methylation status and mRNA levels in all of these breast cancer cell lines examined.

To test for the consequence of promoter methylation on hHIN-1 expression, the effect of a DNA methyltransferase inhibitor (5-aza-2'-deoxycytidine; "5aza-C") on hHIN-1 mRNA levels was analyzed. Six breast cancer cell lines with no detectable expression of hHIN-1 were grown in the presence or absence of 25 µM 5aza-C for three to ten days, then lysed for RNA and DNA preparation. The expression of hHIN-1 mRNA was determined by RT-PCR analysis, while the extent of promoter methylation was evaluated by sequence analysis of bisulfite treated genomic DNA. As shown in FIG. 6A, 5aza-C treatment lead to the re-expression of hHIN-1 mRNA in all six cell lines. This hHIN-1 re-expression correlated with a decrease in the extent of promoter methylation (FIG. 6A; compare the degree of hHIN-1 promoter region methylation in ZR-75-1 cells not treated with 5aza-C ("ZR-75-1") and ZR-75-1 cells treated with 5aza-C ("ZR-75-1-AC")). Based on these data, it is concluded that methylation is at least partially responsible for the loss of hHIN-1 expression in breast cancer cell lines.

A methylation specific PCR (MSP) assay was developed in order to analyze the methylation status of the hHIN-1 promoter region in primary breast tumors. Primers were designed to amplify methylated or un-methylated DNA following bisulfite treatment. Using this approach, the HIN-1 promoter regions of three independent normal breast tissues were found to be completely unmethylated, while that of a positive control breast cancer cell line (ZR75-1) was completely methylated. Analysis of 28 cell lines and 101 primary tumors showed that the hHIN-1 promoter regions of 89% of the cell lines and 74% of primary tumors were completely or partially methylated (representative examples are shown in FIG. 6C). Of these primary tumors, 31 (23 methylated and 8 unmethylated) were analyzed by real-time PCR. All of the methylated tumors and 6 of the unmethylated ones lacked hHIN-1 mRNA. These results indicate that aberrant hHIN-1 promoter region hypermethylation and subsequent lack of expression occur frequently in breast cancers. However, other mechanisms might be responsible for silencing hHIN-1 in a small fraction of tumors. Whether hHIN-1 promoter region hypermethylation in the tumors correlates with any patient or tumor characteristics was analyzed. The results are summarized in Table 1. Among the parameters analyzed, only the association of lack of hHIN-1 promoter region hypermethylation with high histologic grade appeared to be statistically significant. The lack of hHIN-1 promoter region methylation coupled with the lack of hHIN-1 expression observed in these high-grade tumors indicates that in the high histologic grade tumors either (1) hHIN-1 expression is silenced by some mechanism other than promoter region hypermethylation, e.g., loss of a crucial transcription factor or that (2) there is a deficiency in a downstream mediator of the hHIN-1 signaling pathway. Since high-grade tumors in general have worse overall prognosis, hHIN-1 promoter region methylation status may predict the clinical behavior of tumors.

TABLE 1 hHIN-1 promoter region methylation status in breast cancers with various characteristics and from patients of different ages.

| HIN-1 Methylation | Yes Number (% of total) | No Number (% of total) | Total Number |
|---|---|---|---|
| Patients | 73 (72) | 28 (28) | 101 |
| Age, y | | | |
| ≧40 | 60 (70) | 26 (30) | 86 |
| ≦40 | 12 (86) | 2 (14) | 14 |
| ≧50 | 33 (67) | 16 (33) | 49 |
| ≦50 | 39 (76) | 12 (24) | 51 |

TABLE 1-continued hHIN-1 promoter region methylation status in breast cancers with various characteristics and from patients of different ages.

| HIN-1 Methylation | Yes Number (% of total) | No Number (% of total) | Total Number |
|---|---|---|---|
| Tumors Estrogen receptor (ER) | | | |
| positive | 43 (78) | 12 (22) | 55 |
| negative | 26 (67) | 13 (33) | 39 |
| Progesterone receptor (PR) | | | |
| positive | 39 (80) | 10 (20) | 49 |
| negative | 30 (67) | 15 (33) | 45 |
| ER/PR | | | |
| positive | 34 (79) | 9 (21) | 43 |
| negative | 21 (64) | 12 (36) | 33 |
| Her2/neu/erbB2 | | | |
| positive | 38 (70) | 16 (30) | 54 |
| negative | 27 (77) | 8 (23) | 35 |
| Histology grade | | | |
| high | 26 (60) | 17 (40) | 43 |
| low/intermediate | 35 (80) | 9 (20) | 44 |
| Lymph node status | | | |
| positive | 36 (78) | 10 (22) | 46 |
| negative | 31 (67) | 15 (33) | 46 |

Promoter methylation status was determined by MSP.
The results of two-sided $X^2$ tests for the occurrence of equal frequencies of hHIN-1 promoter region hypermethylation in the indicated subgroups of the indicated patient and tumor groups were as follows: age ($P = 0.22$), estrogen receptor expression ($P = 0.21$), progesterone receptor expression ($P = 0.16$), estrogen receptor expression and progesterone receptor expression ("ER/PR") ($P = 0.13$), Her2/neu expression ($P = 0.48$), histology grade ($P = 0.052$), and lymph node status ($P = 0.35$).

Example 5 hHIN-1 is a Novel Growth Inhibitory Cytokine

In order to investigate the effect of constitutive hHIN-1 expression on mammary cell growth, a mammalian expression construct containing hHIN-1 polypeptide encoding cDNA (pCEP4-HIN-1) was transfected into various breast cancer cell lines. Stable transfectants were selected in the presence of hygromycin for 2 weeks. Cell colonies were visualized by crystal violet staining. hHIN-1 expression led to a dramatic decrease in colony numbers in BT549 cells and to a lesser degree in MDA-MB-435 cells compared to control pCEP4 transfected cells. In contrast, p53 effectively inhibited cell growth in both cell lines. The different effects of hHIN-1 expression on cell growth in the two cell lines indicate that certain cell lines might be non-responsive to hHIN-1 due to some other defect in the hHIN-1 signaling pathway.

To confirm that hHIN-1 is a secreted protein, an immunoblot analysis of cell extracts and media separated from cells transiently transfected with a mammalian expression construct or infected with a recombinant adenovirus expressing a hexahistidine tagged hHIN-1 protein was performed (FIG. 7). Using a rabbit polyclonal anti-hHIN-1 antibody, a ~11 kDa protein was detected in both cell lysates and media from cells expressing hHIN-1 but not in cell lysates or media from control hHIN-1 non-expressing cells. The hHIN-1 protein migrates as a doublet on SDS/Tricine (the buffer use for the SDS-PAGE) gels.

Example 6

Expression of HIN-1 at Different Stages of Development

The UGRP-1 (Uteroglobin related protein-1) gene is related to the HIN-1 gene and is a downstream target of the Nku2.1 homeogene [Niimi et al. (2001) Ann. N.Y. Acad. Sci. 923:43-58]. Based on amino acid sequence and predicted structural homology, both proteins belong to the secretoglobin family of small, secreted proteins [Singh et al. (2000) Ann. N.Y. Acad. Sci. 923:43-58]. Therefore, HIN-1 and UGRP-1 are now also called SCGB3A1 and SCGB3A2 acronyms for secretoglobin 3A1 and 3A2, respectively [Klug et al. (2000) Ann. N.Y. Acad. Sci. 923:348-354]. The silencing of hHIN-1 expression in human breast carcinomas and decreased colony growth of breast cancer cells following overexpression indicate a tumor suppressor role for the HIN-1 gene.

Figure 11A:
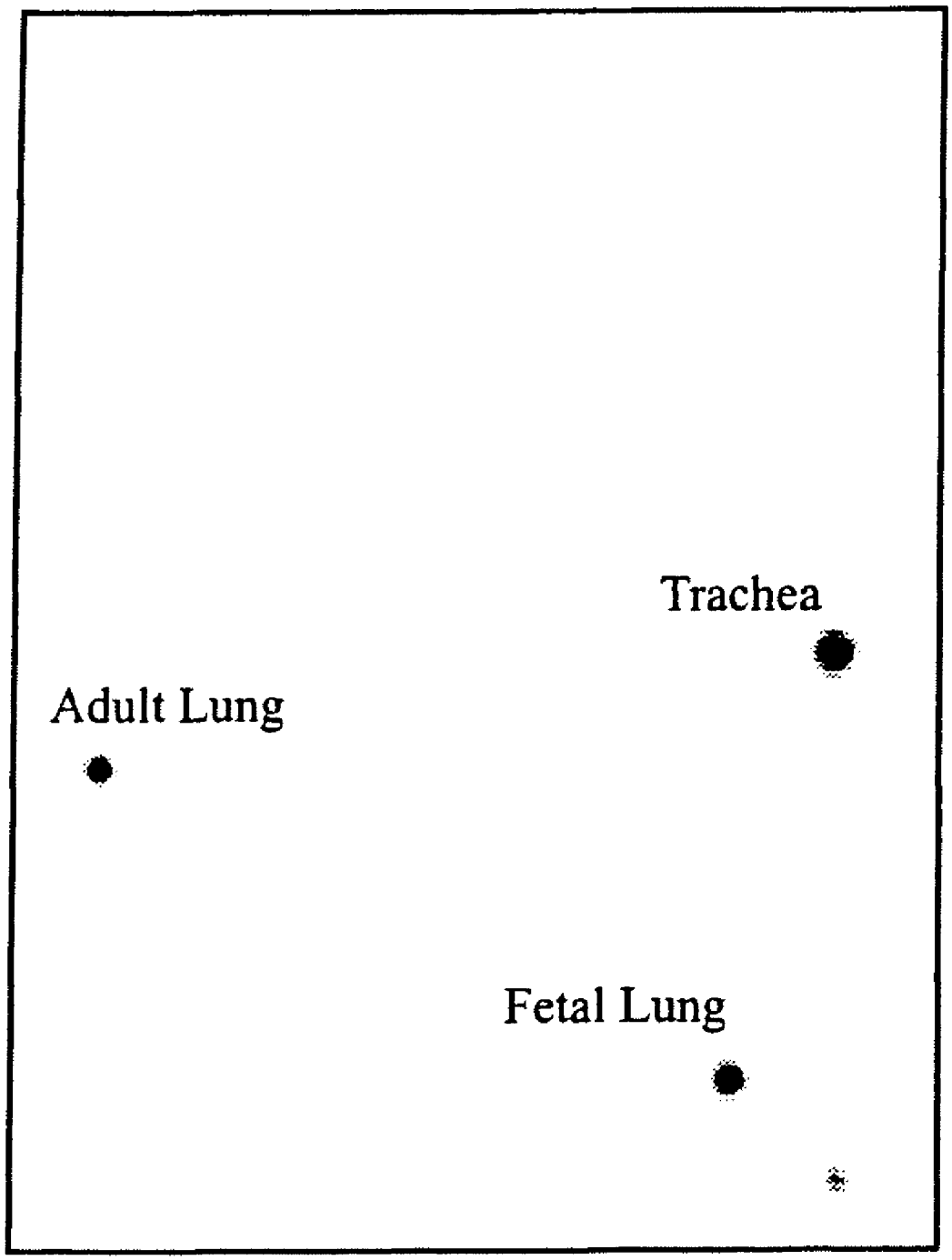
FIG. 11A is a photograph of a dot blot of a 76 human tissue RNA expression array exposed to a human uteroglobin related protein-1 (UGRP-1) cDNA detection probe.
Figure 11B:
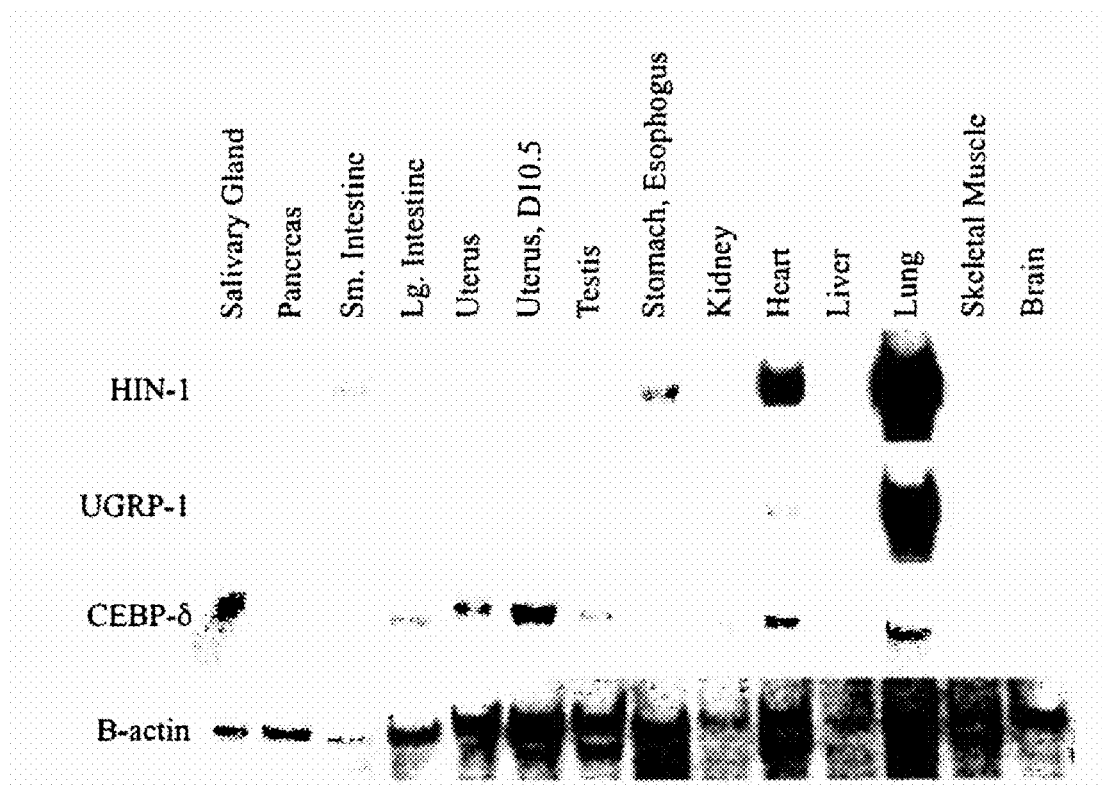
FIGS. 11B and 11C are photographs of Northern blots of RNA from: a variety of adult mouse tissues (FIG. 11B); whole mouse embryos of a variety of embryonic ages (FIG. 11C); and a variety organs from mouse embryos at 18.5 days of embryonic life ("E 18.5") (FIG. 11C) exposed to mouse mHIN-1, mouse UGRP-1, mouse C/EBPδ ("CEBP-δ"), and mouse β-actin cDNA detection probes.
Figure 11C:
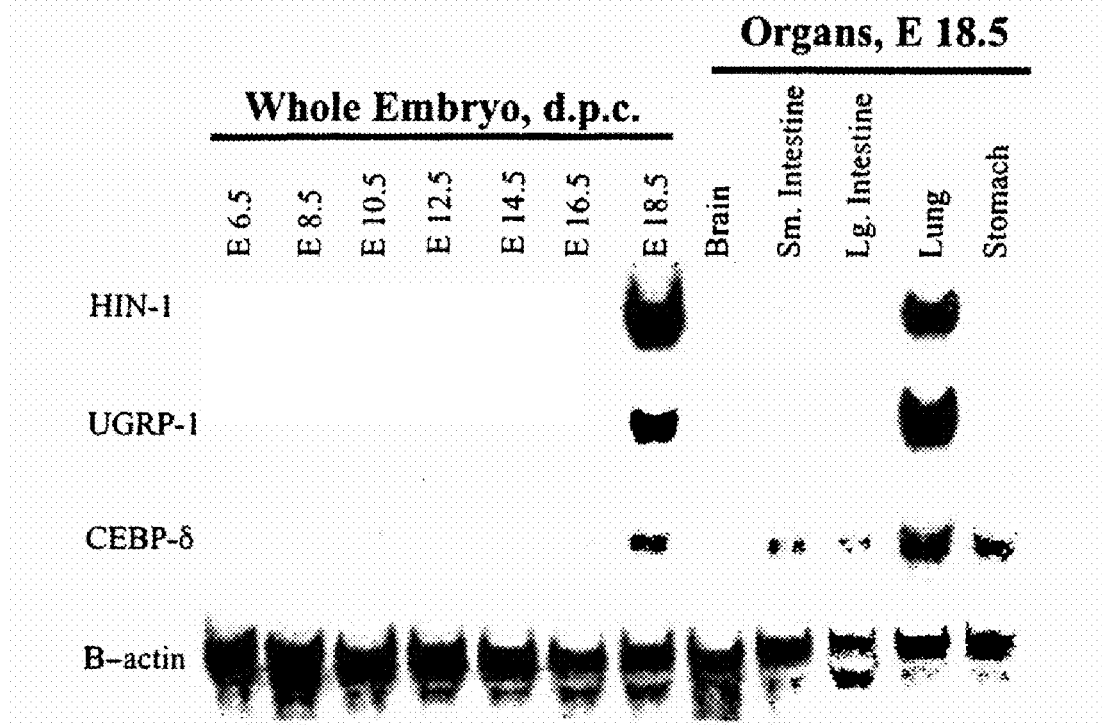
Figure 12A:
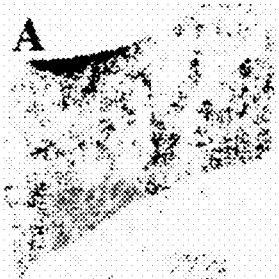
FIGS. 12A-12O are photomicrographs of histological sections of adult (FIGS. 12A-12C) and embryonic (FIGS. 12D-12L) mouse lung and the uterus of a pregnant mouse (FIGS. 2M-12O) exposed to digitonin-labeled mHIN-1 anti-sense and sense (control) RNA probes. Day of embryonic life and the use of the control sense probe are indicated in appropriate figures. The sections shown in FIGS. 12D, 12F, and 12G are transverse sections made at the level of the trachea, the sections shown in FIGS. 12E and 12J are transverse sections made at the level of the bronchi, and the section shown in FIG. 12L is a transverse section made at the level of the bronchioli. Arrows indicate mHIN-1 mRNA expressing cells. Photomicrographs were taken using 2×(FIGS. 12D-12G, 12I, 12J, and 12L), 10×(FIGS. 12A, 12B, 12H, 12K, and 12M-12O), and 20×(FIG. 2C and insets of FIGS. 12L and 12N) objective lenses.
Figure 12B:
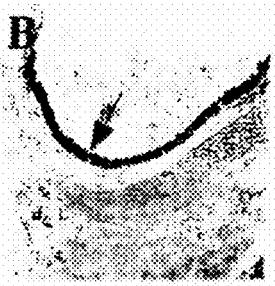
Figure 12C:
Figure 12D:
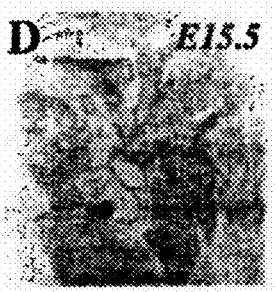
Figure 12E:
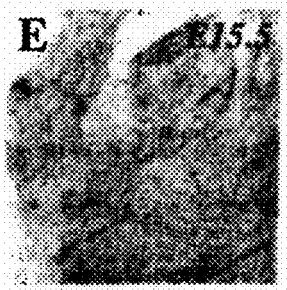
Figure 12F:
Figure 12G:
Figure 12H:
Figure 12I:
Figure 12J:
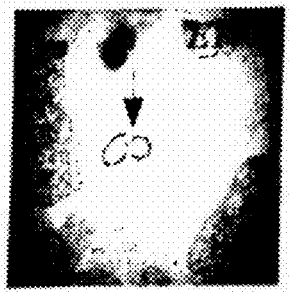
Figure 12K:
Figure 12L:
Figure 12M:
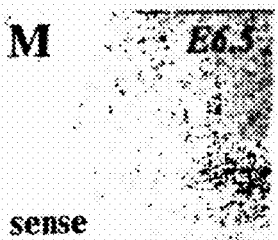
Figure 12N:
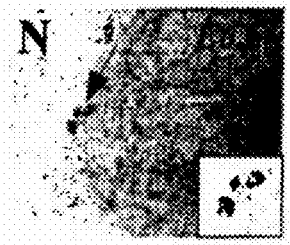

Experiments described above showed that the expression of HIN-1 in humans is restricted to organs composed of branching epithelia. To determine if the expression of UGRP-1 overlaps with that of HIN-1, the expression of both genes was analyzed in various adult and developing human and mouse organs by northern blot hybridization (FIG. 11A-C). In adult organs, UGRP-1 exhibits lung- and trachea-specific expression in both humans and mice (FIGS. 11A and B). While the highest level of mHIN-1 expression is detected in the lung, a low level of expression was also detected in the heart, stomach, and small intestine of the mouse (FIG. 11B). During development of the mouse high mHIN-1 and UGRP-1 expression was first detected in the lung at E17.5-E18.5 (day 17.5 to day 18.5 of embryonic life) (FIG. 11C and FIGS. 12G and H). A low level of mHIN-1 mRNA expression was detectable in embryos at E6.5 (day 6.5 of embryonic life) (FIG. 11C); however, mRNA in situ hybridization revealed that the source of the mHIN-1 mRNA was likely contaminating uterine tissue (FIGS. 12N and O).

Figure 11D:
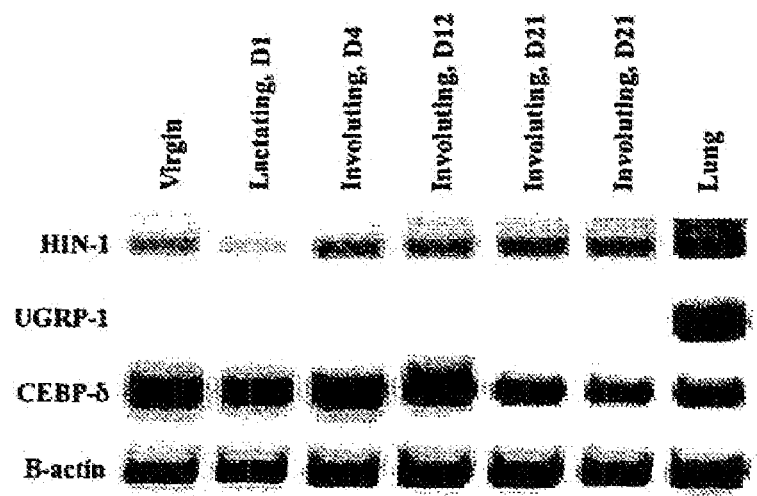
FIGS. 11D and 11E are photographs of ethidium bromide-stained electrophoretic gels of reverse transcriptase-PCR (RT-PCR) reactions performed to detect the presence of mHIN-1 mRNA, mouse UGRP-1 mRNA, mouse C/EBPδ mRNA, and mouse β-actin mRNA in RNA isolated from: mammary glands of virgin female mice and female mice (lactating or involuting) at days 1, 4, 12, and 21 (D1, D4, D12, and D21, respectively) post partum (FIG. 11D); and mammary glands from female mice at days 6.5, 8.5, 10.5, 12.5, 14.5, 16.5, and 18.5 post coitum and mammary glands from lactating female mice at day 1 post partum ("Lactating D1") (FIG. 11E). Control PCR reactions using mouse lung cDNA as a template were also performed ("Lung") (FIGS. 1D and E).
Figure 11E:
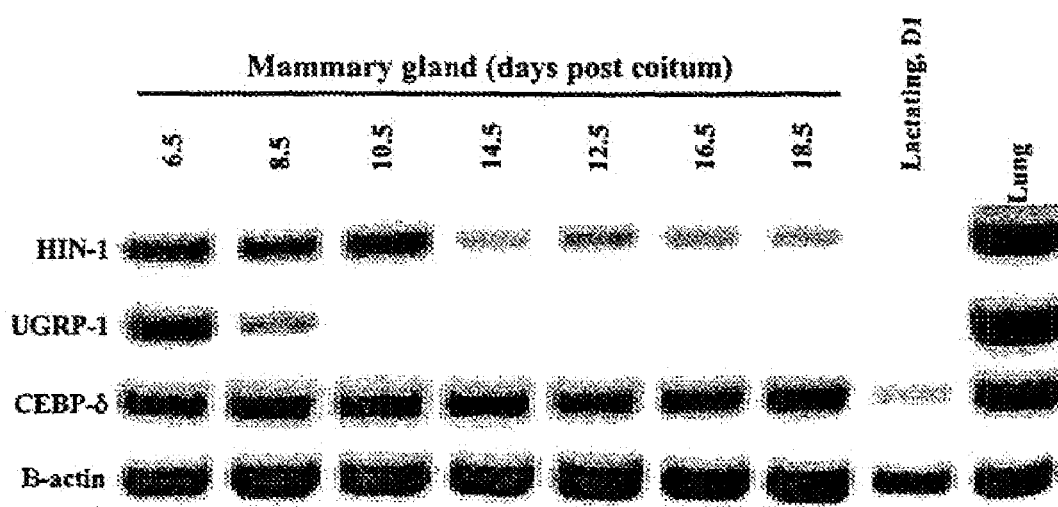

Northern analysis showed no mHIN-1 and UGRP-1 expression in the mouse mammary gland (data not shown). To test for a level of expression below the detection sensitivity of northern analysis, the expression of mHIN-1 and UGRP-1 in the mouse mammary gland at different developmental stages was studied (FIGS. 11D and E). Consistent with the importance of hHIN-1 in human breast carcinomas, expression of both mHIN-1 and UGRP-1 mRNA was observed in the mouse mammary gland. Specifically, the expression of UGRP-1 mRNA is up-regulated in early gestation and then becomes undetectable after day 10.5 p.c. (post coitum). In contrast, after initial up-regulation, mHIN-1 expression was maintained at a low level throughout gestation and lactation, followed by a second increase during involution (FIGS. 11D and E). Since in normal human mammary epithelial cells and in breast carcinomas the expression of hHIN-1 correlated with that of the transcription factor C/EBPδ [Porter et al. (2001) Cancer Res. 61:5697-5702], the levels of C/EBPδ in multiple mouse tissues were analyzed in order to determine if C/EBPδ could be an up-stream regulator of HIN-1 expression. Although C/EBPδ was detected in the tissues at the developmental stages at which mHIN-1 was expressed, the levels of C/EBPδ mRNA did not show a strict correlation with those of mHIN-1 mRNA (FIGS. 11B-E).

Figure 12O:

Experiments described above showed that in the human mammary gland hHIN-1 expression is restricted to luminal mammary epithelial cells. To further analyze the expression of mHIN-1 at the cellular level in the mouse, mRNA in situ hybridization of adult lung, trachea and mouse embryos at different stages of embryogenesis was performed (FIGS. 12A-O and data not shown). mHIN-1 is highly and specifically expressed in the glandular epithelium lining the trachea and in bronchi both in adult mouse lung and in the lungs of embryonic mice at E17.5-E18.5 (FIGS. 12A-L). Similar to UGRP-1, HIN-1 was also expressed in the epithelial cells of pregnant mouse uterine glands (FIGS. 12N and O).

Figure 13:
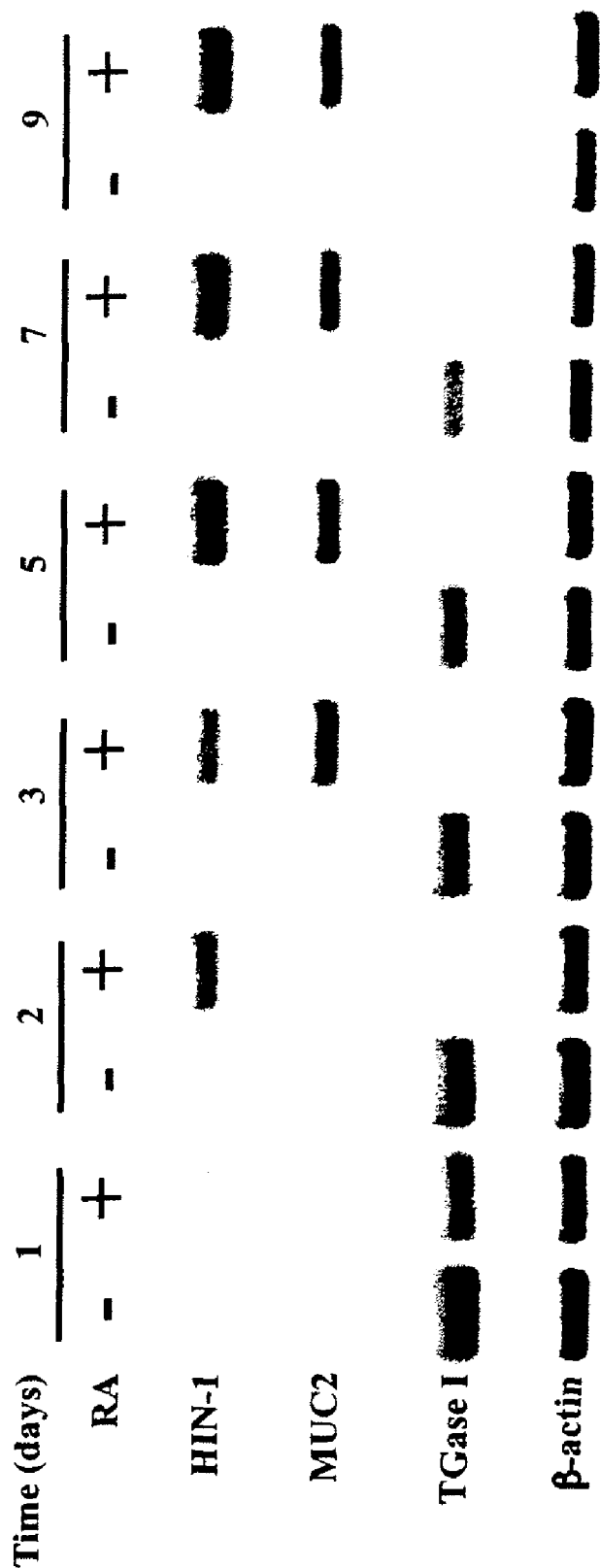
FIG. 13 is a photograph of an ethidium bromide-stained electrophoretic gel of RT-PCR reactions performed to detect the presence hHIN-1 ("HIN-1") mRNA, mucin 2 ("MUC2") mRNA, human squamous cell marker transglutaminase I ("TGase I") mRNA, and human β-actin mRNA in RNA extracted from human primary bronchial epithelial cells cultured with ("+") and without ("−") all-trans-retinoic acid ("RA") for 1, 2, 3, 5, 7, and 9 days.

The above pattern of mHIN-1 expression in adult and developing embryos strongly suggests a role for HIN-1 in terminal differentiation of epithelial cells. To test this hypothesis, the expression of hHIN-1 mRNA by RT-PCR during retinoic acid-induced mucinous differentiation of primary human bronchial epithelial cells was analyzed (FIG. 13). Primary human bronchial epithelial cells underwent squamous epithelial differentiation and expressed squamous cell markers such as transglutaminase I (Tgase I) in the absence of all-trans retinoic acid (FIG. 13). Following retinoic acid treatment in an air-interface culture, human bronchial epithelial cells differentiated into mucinous cells as demonstrated by the expression of genes specific for the mucinous phenotype such as MUC2 (FIG. 13) [Koo et al. (1999) *Am. J. Respir. Cell Mol. Biol.* 20:43-52]. In this in vitro differentiation system the expression of hHIN-1 mRNA correlated with the loss of a squamous marker (Tgase I) and preceded the induction of a marker for mucinous differentiation (MUC2) following retinoic acid treatment. Such expression kinetics are consistent with a role for HIN-1 as an inducer of this process.

Example 7

*Drosophila* Homologues of HIN-1

Figure 14A:
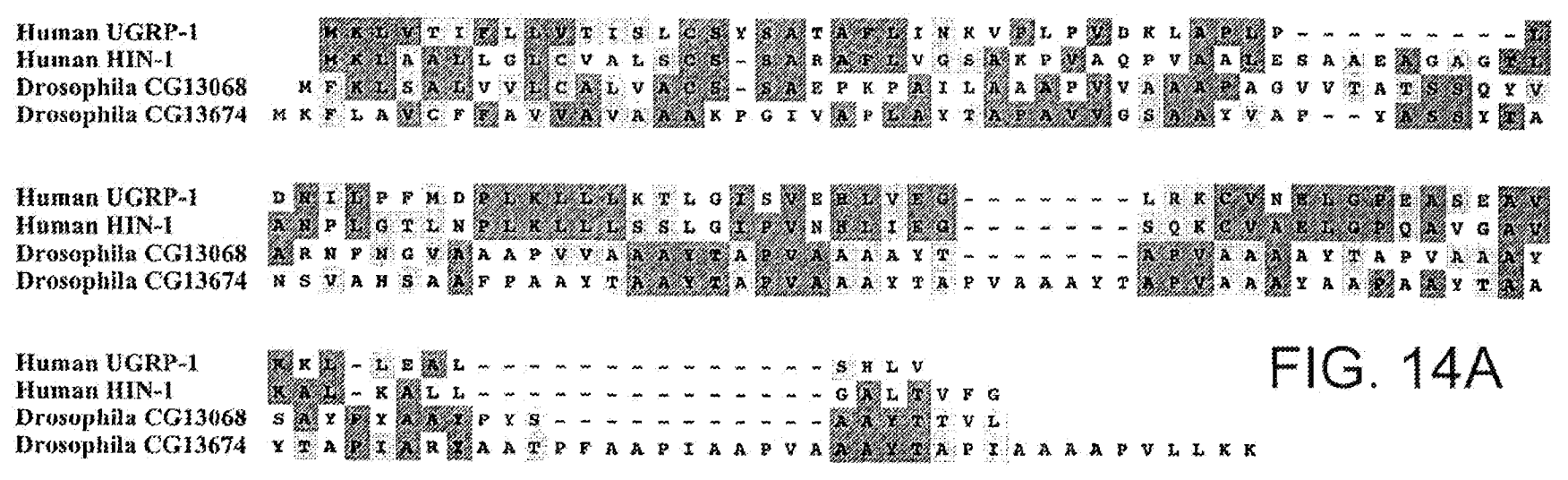
Figure 14B:
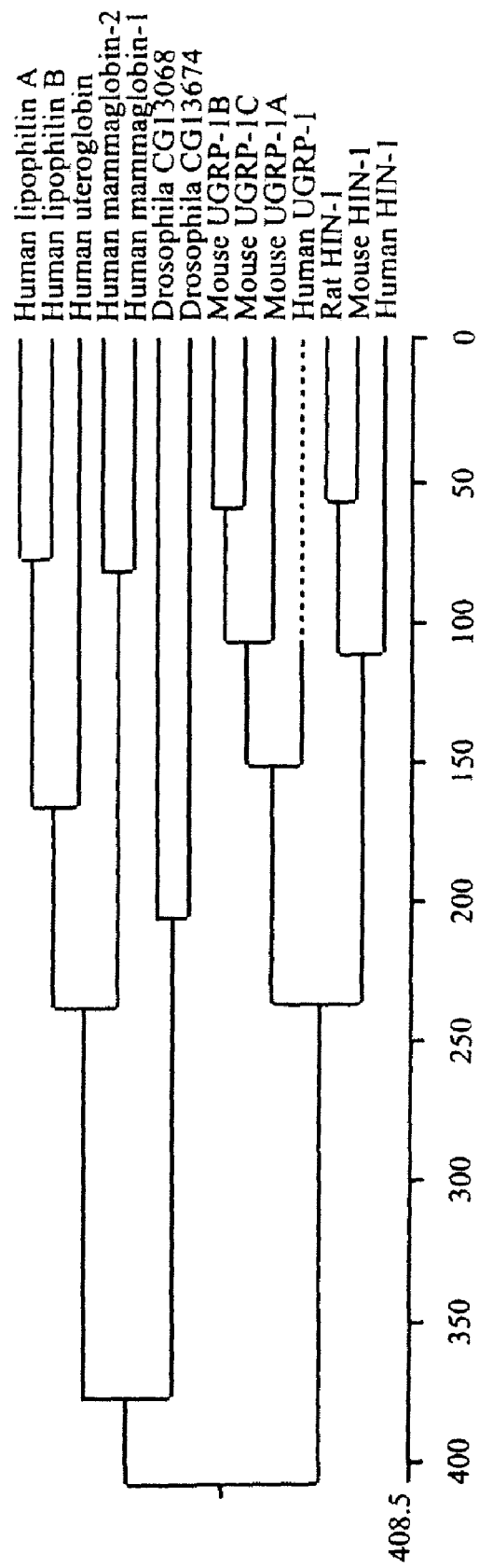
FIG. 14B is a dendrogram generated using DNASTAR3 software and the J. Hein algorithm indicating the phylogenetic relationship of a variety of HIN-1 homologues.

Two previously uncharacterized *Drosophila* proteins (Drosophila genes GC130681 and GC13674) were identified as showing limited (~30%) homology to hHIN-1 and human UGRP-1 (FIG. 14A). The identification of these HIN-1/UGRP-1 homologues is particularly interesting, since to date no secretoglobins have been identified in non-mammalian species. The evolutionary relationship of these *Drosophila* proteins to members of the secretoglobin family is depicted in FIG. 14B.

The amino acid sequence of the GC130681 protein is designated SEQ ID NO:28 and the nucleotide sequence of cDNA encoding the GC130681 protein is designated SEQ ID NO:29 (FIG. 15). The amino acid sequence of the GC13674 protein is designated SEQ ID NO:30 and the nucleotide sequence of cDNA encoding the GC13674 protein is designated SEQ ID NO:31 (FIG. 16). The amino acid sequence of human UGRP-1 is designated SEQ ID NO:32.

To determine if the function of HIN-1 is conserved between mammals and fruit flies, the expression of the GC130681 gene during *Drosophila* development was analyzed by mRNA in situ hybridization. Expression of GC130681 mRNA was detected in the tracheal system of stage 15-16 embryos. This finding correlates well with the above-described studies on mHIN-1 expression during mouse embryo development.

It should be understood that various modifications can be made to the above-described embodiments without departing from the spirit of the invention. Accordingly, the invention is limited only by the following claims.

---

What is claimed is:

1. A method of determining the likelihood of a cancer cell being a high grade cancer cell, the method comprising:
   (a) providing a human cancer test cell;
   (b) determining the methylation status of a HIN-1 promoter region in the test cell; and
   (c) identifying the test cell as being likely to be a high grade cancer cell when the HIN-1 promoter region is unmethylated and identifying the test cell as likely to be a low grade or an intermediate grade cancer cell when the HIN-1 promoter region is methylated or partially methylated.

2. The method of claim 1, wherein the test cell is a breast cancer cell.

3. The method of claim 1, wherein the test cell is selected from the group consisting of a lung cancer cell, a prostate cancer cell, a pancreatic cancer cell, a gastrointestinal cancer cell, and a skin cancer cell.

4. The method of claim 1, wherein determining the methylation status comprises a methylation-specific polymerase chain reaction (MCP) assay.

5. The method of claim 1, wherein the HIN-1 promoter region comprises a nucleotide sequence in a genomic segment, the genomic segment comprising (i) a HIN-1 5' promoter region (SEQ ID NO: 19) and (ii) the first twelve nucleotides of SEQ ID NO:3.

6. The method of claim 5, wherein the nucleotide sequence comprises nucleotide 1 to nucleotide 252 of SEQ ID NO:19.

7. The method of claim 5, wherein the nucleotide sequence consists of nucleotide 1 to nucleotide 252 of SEQ ID NO:19.

8. The method of claim 5, wherein the nucleotide sequence comprises nucleotide 229 to nucleotide 551 of SEQ ID NO:19 and nucleotide 1 to nucleotide 12 of SEQ ID NO:3.

9. The method of claim 5, wherein the nucleotide sequence consists of nucleotide 229 to nucleotide 551 of SEQ ID NO:19 and nucleotide 1 to nucleotide 12 of SEQ ID NO:3.

10. The method of claim 5, wherein the nucleotide sequence comprises SEQ ID NO:19 and nucleotide 1 to nucleotide 12 of SEQ ID NO:3.

11. The method of claim 5, wherein the nucleotide sequence consists of SEQ ID NO:19 and nucleotide 1 to nucleotide 12 of SEQ ID NO:3.

* * * * *